(12) United States Patent
Muraki et al.

(10) Patent No.: US 7,601,843 B2
(45) Date of Patent: *Oct. 13, 2009

(54) 4-(2-FUROYL)AMINOPIPERIDINE COMPOUND USEFUL AS THERAPEUTIC AGENT FOR ITCHING

(75) Inventors: Yukiko Muraki, Fujimino (JP); Tomokazu Fujimoto, Nara (JP); Takuya Kishimoto, Fujimino (JP)

(73) Assignees: Kyorin Pharmaceutical Co., Ltd, Tokyo (JP); Nisshin Seifun Group Inc., Tokyo (JP)

( * ) Notice: Subject to any disclaimer, the term of this patent is extended or adjusted under 35 U.S.C. 154(b) by 336 days.

This patent is subject to a terminal disclaimer.

(21) Appl. No.: 10/555,635

(22) PCT Filed: May 6, 2004

(86) PCT No.: PCT/JP2004/006421

§ 371 (c)(1), (2), (4) Date: Nov. 4, 2005

(87) PCT Pub. No.: WO2004/099194

PCT Pub. Date: Nov. 18, 2004

(65) Prior Publication Data

US 2006/0270632 A1    Nov. 30, 2006

(30) Foreign Application Priority Data

May 8, 2003   (JP)   ............................. 2003-130634

(51) Int. Cl.
C07D 211/68    (2006.01)
A61K 31/445    (2006.01)
(52) U.S. Cl. ..................... 546/194; 514/318
(58) Field of Classification Search ............... 546/194; 514/318
See application file for complete search history.

(56) References Cited

U.S. PATENT DOCUMENTS

| | | | |
|---|---|---|---|
| 5,667,773 A | 9/1997 | Farrar et al. | 424/78.05 |
| 5,798,093 A | 8/1998 | Farrar et al. | 424/45 |
| 5,811,078 A | 9/1998 | Maycock et al. | 424/45 |
| 5,888,494 A | 3/1999 | Farrar et al. | 424/78.05 |
| 2003/0004340 A1 | 1/2003 | Gibson et al. | 544/60 |
| 2005/0085508 A1 | 4/2005 | Fukutomi et al. | 514/318 |

FOREIGN PATENT DOCUMENTS

WO    WO 03/035645 A1    5/2003

OTHER PUBLICATIONS

Silverman, R. B. The Org. Chem. Of Drug Design and Drug Action, Academic Press, Inc.: San Diego, 1992, pp. 4-51.*
Andoh, et al., *Inhibitory Effects of Azelastine on Substance P-induced Itch-associated Response in Mice*, European Journal of Pharmacology, Dec. 21, 2001, 436 (2002), pp. 235-239.
Andoh, et al., *Substance P Induction of Itch-Associated Response Mediated by Cutaneous NK Tachykinin Receptors in Mice*, The Journal of Pharmacology and Experimental Therapeutics, Apr. 13, 1998, vol. 286 No. 3 (1998), pp. 1140-1145.

* cited by examiner

Primary Examiner—Rebecca L Anderson
Assistant Examiner—Robert Havlin
(74) Attorney, Agent, or Firm—Ohlandt, Greeley, Ruggiero & Perle, L.L.P.

(57) ABSTRACT

There are provided compounds represented by the following general formula (I):

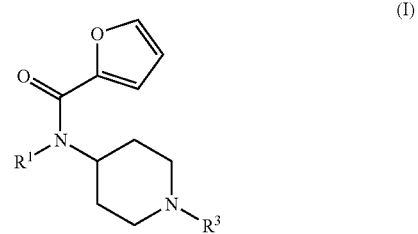

(I)

[where $R^1$ is 5-methylpyridin-2-yl, p-tolyl or mesityl, $R^2$ is one of the following general formulas (II)-(IX):

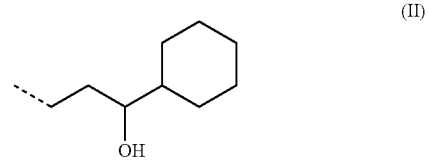

(II)

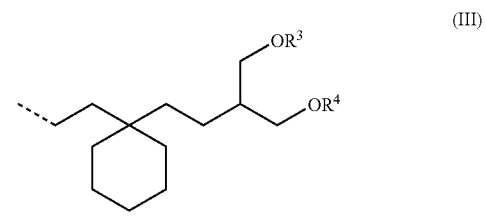

(III)

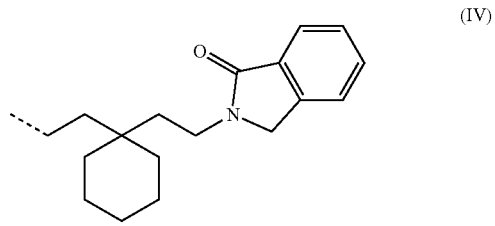

(IV)

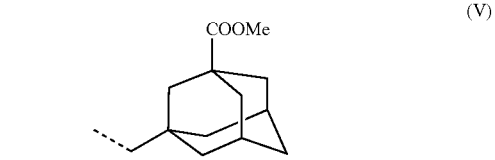

(V)

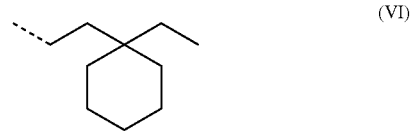

(VI)

-continued

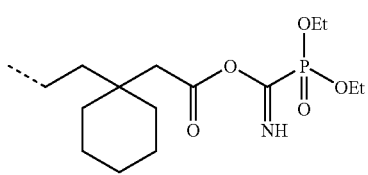
(VII)

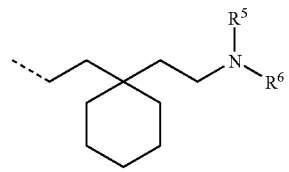
(VIII)

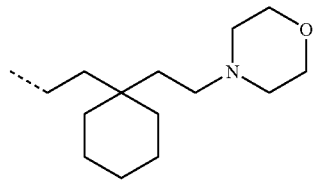
(IX)

(where $R^3$ is C1-C4 alkyl, $R^4$ is H or C1-C4 alkyl, $R^5$ is H, 3-pyridylmethyl or 4-pyridylmethyl, and $R^6$ is 2,4-dihydroxybenzyl, 3-pyridylmethyl or 4-pyridylmethyl), or when $R^1$ is mesityl, $R^2$ is the following formula (X)],

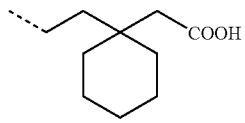
(X)

and pharmaceutically acceptable salts thereof. The compounds exhibit pruritus-inhibiting action, and are useful for prevention or of itching and pruritus caused by reaction against insect-inflicted wounds, reaction against environmental allergens, skin infections or external parasite infections, or caused to renal dialysis patient.

4 Claims, No Drawings

4-(2-FUROYL)AMINOPIPERIDINE COMPOUND USEFUL AS THERAPEUTIC AGENT FOR ITCHING

TECHNICAL FIELD

The present invention relates to novel 4-(2-furoyl)aminopiperidine compounds which are useful as therapeutic agents for pruritus, as well as to a process for their production and their use as medicines.

DISCUSSION OF THE BACKGROUND ART

Opioid receptors are the target receptors of specific binding by drugs with morphine-like activity, and such receptors are present in the central nervous system and enteric nervous system. Three types of opioid receptors are known, μ, δ and κ. The opioid μ receptors are associated with analgesia, respiratory depression, euphoria, psychosomatic dependence, tolerance, enterokinetic inhibition, bradycardia, constipation and miosis. On the other hand, the opioid δ receptors are associated with analgesia, psychosomatic dependence and emotion, while opioid κ receptors are associated with analgesia, sedation, bradycardia, diuresis, aversion and miosis.

WO03/035645 describes 4-(2-furoyl)aminopiperidine derivatives which act as opioid μ receptor antagonists. Because this group of compounds exhibit strong opioid μ receptor antagonism and are selective for peripheral regions, they are useful as therapeutic agents for enterokinetic disorders such as constipation and irritable bowel syndrome. However, although the group of compounds exhibit powerful opioid μ receptor antagonism and have been effective against the side-effects of opioid μ receptor agonists such as constipation, nausea and vomiting, or against idiopathic constipation, postoperative ileus, paralytic ileus and irritable bowel syndrome, they have either failed to produce any effect or a satisfactory effect against itching or pruritus, and therefore more powerful therapeutic agents for itching or pruritus have been desired. US Patent Publication US2003-004340A also teaches that compounds that bind to opiate receptors (for example, μ, κ and δ receptors) are useful for treatment of itching or pruritus.

SUMMARY OF THE INVENTION

As a result of diligent research directed toward providing compounds exhibiting a powerful therapeutic effect against itching or pruritus without side-effects, the present inventors have discovered that a powerful therapeutic effect on itching or pruritus is exhibited by compounds represented by the following general formula (I):

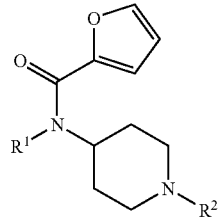

(I)

[where $R^1$ is 5-methylpyridin-2-yl, p-tolyl or mesityl, $R^2$ is one of the following general formulas (II)-(IX):

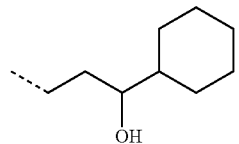

(II)

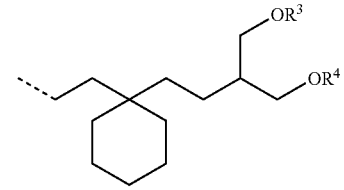

(III)

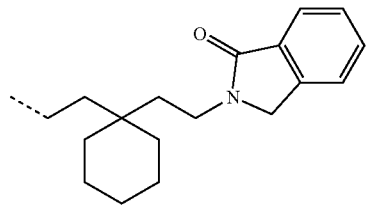

(IV)

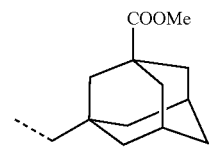

(V)

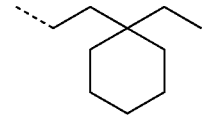

(VI)

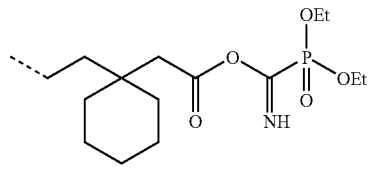

(VII)

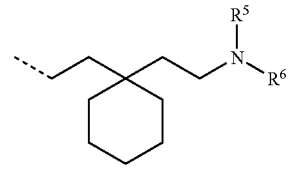

(VIII)

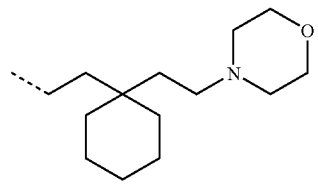

(IX)

(where $R^3$ is C1-C4 alkyl, $R^4$ is H or C1-C4 alkyl, $R^5$ is H, 3-pyridylmethyl or 4-pyridylmethyl, and $R^6$ is 2,4-dihy droxybenzyl, 3-pyridylmethyl or 4-pyridylmethyl), or when R¹ is mesityl, R² is the following formula (X)],

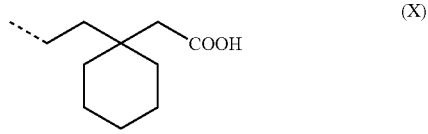

whose structure is a partially modified structure of the 4-(2-furoyl)aminopiperidine derivatives disclosed in WO03/035645, as well as pharmaceutically acceptable salts thereof.

Examples of compounds included by general formula (I) include:

N-[1-[2-[1-[2-[bis(pyridin-3-ylmethyl)amino]ethyl]cyclohexyl]ethyl]piperidin-4-yl]-N-(p-tolyl)-2-furancarboxamide, N-[1-[2-[1-[2-[bis(pyridin-4-ylmethyl)amino]ethyl]cyclohexyl]ethyl]piperidin-4-yl]-N-(p-tolyl)-2-furancarboxamide, N-[1-[2-[1-[2-(1-oxo-2-isoindolinyl)ethyl]cyclohexyl]ethyl]piperidin-4-yl]-N-(p-tolyl)-2-furancarboxamide, N-[1-[2-[1-[2-(2,4-dihydroxybenzylamino)ethyl]cyclohexyl]ethyl]piperidin-4-yl]-N-(p-tolyl)-2-furancarboxamide, N-[1-[2-[1-[2-(morpholino)ethyl]cyclohexyl]ethyl]piperidin-4-yl]-N-(p-tolyl)-2-furancarboxamide, N-[1-(3-cyclohexyl-3-hydroxypropyl)piperidin-4-yl]-N-(5-methylpyridin-2-yl)-2-furancarboxamide, N-[1-[(3-methoxycarbonyl-1-tricyclo[3.3.1.1$^{3,7}$]decyl)methyl]piperidin-4-yl]-N-(5-methylpyridin-2-yl)-2-furancarboxamide,

[1-[2-[4-[N-(5-methylpyridin-2-yl)-2-furancarboxamide]piperidin-1-yl]ethyl]cyclohexyl]acetic diethylphosphonocarboximidic anhydride,

[1-[2-[4-(N-mesityl-2-furancarboxamide)piperidin-1-yl]ethyl]cyclohexyl]acetic acid, N-[1-[2-(1-ethylcyclohexyl)ethyl]piperidin-4-yl]-N-(5-methylpyridin-2-yl)-2-furancarboxamide, N-[1-[2-[-(4-methoxy-3-methoxymethylbutyl)cyclohexyl]ethyl]piperidin-4-yl]-N-(5-methylpyridin-2-yl)-2-furancarboxamide, N-[1-[2-[1-(4-methoxy-3-hydroxymethylbutyl)cyclohexyl]ethyl]piperidin-4-yl]-N-(5-methylpyridin-2-yl)-2-furancarboxamide, and their pharmaceutically acceptable salts.

The compounds of the invention having at least one asymmetric center can exist as enantiomers and diastereomers. Diastereoisomers can be separated by conventional methods such as fractional crystallization or chromatography. Various stereoisomers can be isolated by separation of racemic mixtures or other mixtures of the compounds using conventional techniques such as fractional crystallization or HPLC. Desired optical isomers may be prepared by reaction with appropriate optically active starting materials under conditions that do not promote racemization or epimerization. Alternatively, a desired optical isomer may be prepared through resolution by HPLC of a racemic form using a suitable chiral support, or when appropriate, by fractional crystallization of a diastereoisomer formed by reaction between a suitable optically active acid or base and the racemic form. The invention encompasses both individual separated isomers and isomer mixtures.

All protected derivatives, prodrugs and active metabolites of the compounds represented by general formula (I) are also included within the scope of the invention.

The compounds of the invention may be produced by methods similar to the production methods for 4-(2-furoyl) aminopiperidine derivatives disclosed in WO03/035645.

Medically acceptable acid addition salts of the compounds represented by general formula (I) according to the invention may be produced by ordinary methods. For example, solutions of free bases are reacted with suitable acids either directly or in appropriate solvents, and then the obtained salts are filtered or the reaction solvents are evaporated off under reduced pressure, for isolation. Also, medically acceptable base addition salts may be obtained by treatment of solutions of the compounds represented by general formula (I) according to the invention with appropriate bases, by the same methods. Both types of salts may be formed or interconverted using ion-exchange resin techniques. As examples of acid addition salts there may be mentioned salts with inorganic acids such as hydrochloric acid, hydrobromic acid, sulfuric acid and phosphoric acid, and salts with organic acids such as acetic acid, succinic acid, oxalic acid, malic acid, tartaric acid, fumaric acid, maleic acid, citric acid, malonic acid, lactic acid, methanesulfonic acid, p-toluenesulfonic acid, mandelic acid, suberic acid, phthalic acid and terephthalic acid, while as base addition salts there may be mentioned salts with inorganic and organic bases such as sodium salts, potassium salts and various ammonium salts.

The aforementioned compounds of the invention are useful for curative treatment or prophylactic treatment of itching and pruritus in animals and humans. Itching, or pruritus, is a common dermatological syndrome responsible for considerable suffering in both humans and animals, and itching is known to accompany both endogenous and exogenous conditions. As endogenous and exogenous conditions there may be mentioned chronic renal insufficiency, primary biliary cirrhosis, biliary obstruction, biliary stasis, hepatitis, polycythemia vera, lymphoma, leukemia, Hodgkin's disease, multiple myeloma, iron deficiency, mastocytosis, hyperthyroidism, hypothyroidism, carcinoid syndrome, diabetes, malignant tumor, psychopathy, helminth infection, xeroderma, scabies, herpetiform dermatitis, atopic dermatitis, simple chronic lichen, psoriasis, lichen planus, contact dermatitis, sudamen, insect sting, urticaria, folliculitis, sunburn, polymorphous light eruption, bullous pemphigoid, fungal infection, mycosis fungoides, seborrheic dermatitis, and the like.

The compounds of the invention are particularly useful for curative treatment or prophylactic treatment of itching and pruritus caused by pruritic skin diseases such as allergic dermatitis and atopic dermatitis in animals and humans, as well as dialysis patient pruritus, contact dermatitis, psoriasis, eczema and insect sting.

Moreover, by inhibiting the opioid μ receptor, the compounds of the invention are also expected to exhibit effects as therapeutic and prophylactic agents against the side-effects of opioid μ receptor agonists such as constipation, nausea and vomiting, or against idiopathic constipation, postoperative ileus, paralytic ileus and irritable bowel syndrome.

When used as medicines, the compounds represented by general formula (I) may be prepared into a variety of dosage forms. Specifically, a preparation may be administered orally in the form of tablets, sugar-coated tablets, hard capsules, soft capsules, enteric coated preparation, solutions, emulsions, suspensions, or other liquid forms. For parenteral administration, it may be administered in the form of an injection, suppository, enema, solution, emulsion, suspension or other liquid forms. It may also be administered in the form of a topical capsule-forming composition as disclosed in US Patent Publication U.S. Pat. Nos. 5,567,773 and 5,888,494, or a spray formulation as disclosed in U.S. Pat. Nos. 5,798,093 and 5,811,078.

The compounds of the invention may be administered alone, or in combination with one or more drugs used for treatment or prevention of diseases, or for alleviation or suppression of their symptoms. Examples of such drugs include (but should not be considered limited to) antiparasitic drugs such as fipronil, lufenuron, imidacloprid, avermectins (for example, abamectin, ivermectin, doramectin), milbemycin, organic phosphoric acid esters and pyrethroids; antihistamines such as chlorpheniramine, trimeprazine, diphenhydramine and doxylamine; antifungal agents such as fluconazole, ketoconazole, itraconazole, griseofulvin and amphotericin B; antimicrobial agents such as enroflaxacin, marbofloxacin, ampicillin and amoxicillin; anti-inflammatory agents such as prednisolone, betamethasone, dexamethasone, caprofen and ketoprofen; dietary supplements such as γ-linoleic acid; and emollients. Thus, the present invention further provides products which are formulated as combinations of compounds of the invention and compounds in the foregoing list, and such products may be used simultaneously, separately or continuously for treatment of diseases mediated by opiate receptors.

For preparation of such formulations, additives commonly used for drug formulation may be added, such as excipients, stabilizers, fungicides, solubilizing agents, humectants, emulsifiers, lubricants, sweeteners, coloring agents, flavorings, tonicity regulators, buffering agents, antioxidants and the like.

The method and dosage for administration of an opioid μ receptor antagonist according to the invention may be appropriately selected depending on the preparation form, the gender of the patient and the severity of the condition, but the dosage of the active ingredient per day is 1-1000 mg.

DETAILED DESCRIPTION OF THE PREFERRED EMBODIMENT

Measurement results for biological activity of compounds of the invention are shown below.

1. Examination of Effect on Scratching Behavior

The inhibitory effects of the compounds of the invention on scratching behavior were measured using a mouse Substance P induced scratching model (measurement method described by T. Andoh et al., The Journal of Pharmacology and Experimental Therapeutics Vol. 286, No. 3, 1140-1145(1998) and T. Andoh et al., European Journal of Pharmacology Vol. 436 (2002) 235-239). Mice (ICR, 6-week-old, male) were shaven on the rostral dorsum under light ether anesthesia at least one day prior to the experiment, and magnets (1 mm diameter×3 mm) were inserted subcutaneously into both hind limbs. On the day of the experiment, 10 mg/kg of a compound of the invention or a compound described in WO03/035645 was administered (intraabdominally or orally) to each mouse, and after 30 minutes, 100 nmol/site (50 μL) of Substance P was intradermally injected into the rostral dorsum under light ether anesthesia. Beginning two minutes after administration of Substance P, the scratching behavior was recorded for 30 minutes using a scratching behavior measuring system (NS-SCT16, Neuroscience Co., Ltd.) and MicroAct (Data management/recording and analysis software, Neuroscience). The obtained data were analyzed under conditions with 0.05 V Threshold, 0.05 sec Event Gap, 20.00 Hz Max Frequency, 5.00 Hz Min Frequency, 0.30 sec Min Duration. The scratching frequency inhibition (%) was calculated as the average number of scratchings in the invention compound-administered group with respect to the average number of scratchings in the control (solvent) group during 30 minutes. Groups exhibiting a greater frequent of scratching than the control group were indicated as −X %. The scratching frequency inhibition (%) by each of the compounds is shown in Table 1. For comparison, the inhibitory effects of the following compounds on scratching behavior described in WO03/035645 are also shown.

Compounds described in WO03/035645

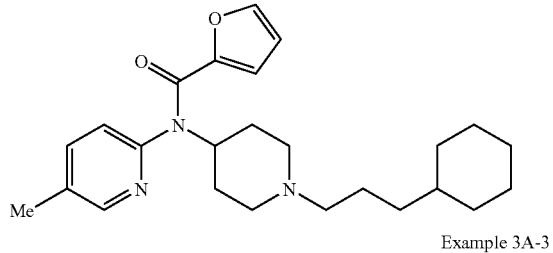

Example 2-3

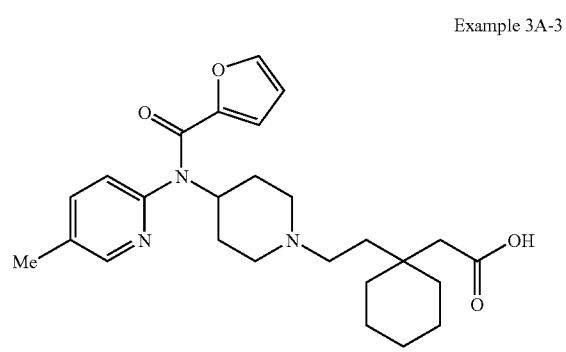

Example 3A-3

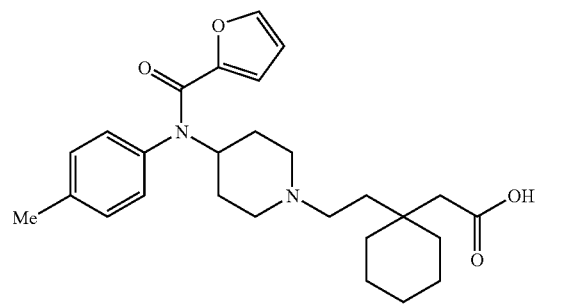

Example 3B-1

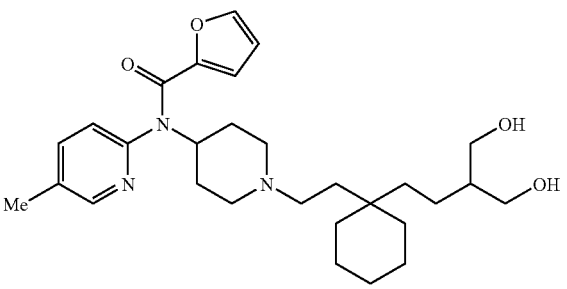

Example 3G-2

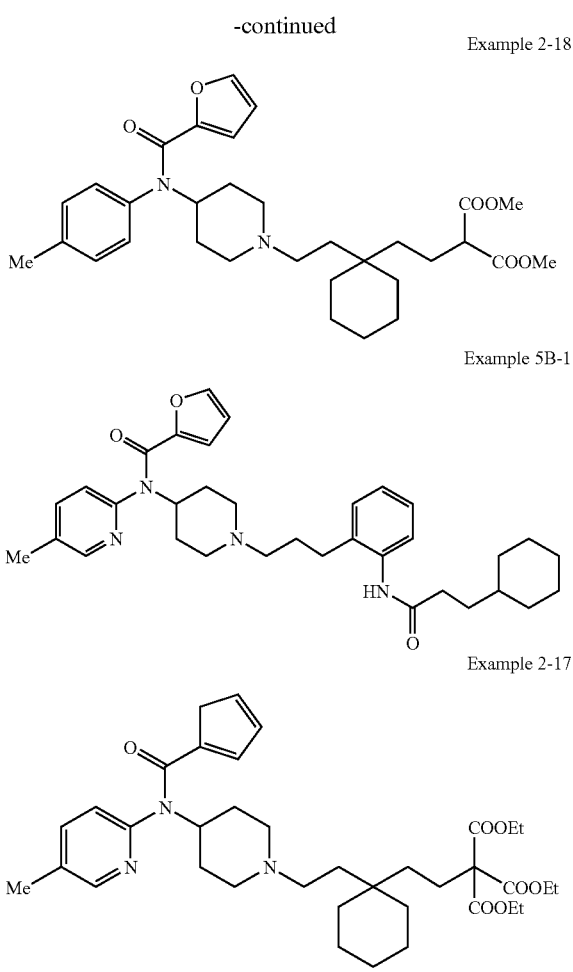

Example 2-18

Example 5B-1

Example 2-17

TABLE 1

Measurement of inhibitory effect on scratching behavior

| | Inhibition (%) | |
|---|---|---|
| Example No. | Intraabdominal administration | Oral administration |
| Example 1-2 | 57 | 31 |
| Example 2-2 | 54 | |
| Example 3-2 | 50 | 55 |
| Example 4 | 35 | |
| Example 5-7 | 45 | |
| Example 6-4 | 50 | 51 |
| Example 7-3 | 54 | |
| Example 8 | 50 | 26 |
| Example 9-5 | 62 | |
| Example 10-8 | 48 | 19 |
| Example 11-1 | 45 | 48 |
| Example 11-2 | 37 | 19 |
| WO03/035645 Ex 2-3 | −50 | |
| WO03/035645 Ex 3A-3 | −23 | |
| WO03/035645 Ex 3B-1 | 23 | |
| WO03/035645 Ex 3G-2 | 25 | |
| WO03/035645 Ex 2-18 | 4 | |
| WO03/035645 Ex 5B-1 | 17 | |
| WO03/035645 Ex 2-17 | 15 | |

These results demonstrate that the compounds of the invention have very strong inhibitory effects on scratching behavior compared to the compounds described in WO03/035645.

2. Examination of Effect on Spontaneous Motility

The effects on mouse spontaneous motility were examined. Six-week-old male ICR mice were used for the test. A compound of the invention was dissolved in distilled water or 20% cremophor EL (SIGMA General Catalog #C5135, Sigma-Aldrich) and intraabdominally administered at a dose of 10 mg/kg. The spontaneous motility was evaluated using an animex apparatus (Scanet MV-20 MT, Melquest Co., Ltd.) from 30 minutes after administration. A plastic cage (W220× D320×H135 mm) was placed in the measuring apparatus, and 30 minutes after administration, the mouse was placed in the cage and observed while measuring for 30 minutes, recording a count representing the total movement of the mouse. The spontaneous motility of the control group (distilled water or 20% cremophor EL) was defined as 100%, and the inhibition was calculated from the average value for the spontaneous motility of each of the administered compounds. The spontaneous motility inhibitions for each of the compounds are shown in Table 2.

TABLE 2

Spontaneous motility inhibition

| Compound No. | Inhibition (%) |
|---|---|
| Example 3-2 | 8.7 |
| Example 6-4 | −19.2 |
| Example 7-3 | 16.7 |
| Example 9-5 | 19.9 |
| Example 10-8 | 16.5 |
| Example 11-2 | −23.8 |

These results demonstrate that the inhibitory action of the compounds of the invention on scratching behavior is not a side-effect caused by depression of spontaneous motility (sedation).

3. Antagonism for Opioid μ Receptors

The opioid μ receptor antagonistic activity ($pA_2$ value) of compounds of the invention was measured by electrical field stimulated longitudinal muscle-myenteric plexus (LMMP) specimen of guinea pig ileum.

The LMMP was prepared by extraction of the ileum after lethal bleeding of a guinea pig (Hartley, male). The specimen was suspended in a Magnus apparatus filled with 20 ml of nutrient solution (Krebs-Henselite solution, 37° C., 95% $O_2$-5% $CO_2$ aeration) with a resting tension of 0.5 g, and the isometric contraction was recorded. After equilibrating the specimen for at least an hour with the nutrient solution, it was subjected to electrical field stimulation (0.1 Hz, 1 msec duration) with a voltage producing the maximum contraction. The opioid μ receptor agonist morphine was added cumulatively after stabilization of contraction, and after washing, the addition was paused for 1 hour. After resuming electrical field stimulation and after stabilization of contraction the compound of the invention was added, and then after 15 minutes morphine was cumulatively added. The contraction height (mm) before and after morphine addition was measured from a chart recording the electrical field stimulation contraction, and the contraction inhibition (%) was calculated using the following Formula 1.

Contraction inhibition (%)=[(a−b)/a]×100    Formula 1 a: Contraction height before morphine addition (mm)
b: Contraction height after morphine addition (mm)

The data were plotted with the morphine logarithmic concentration on the horizontal axis and the contraction inhibition (%) on the vertical axis, to draw a morphine concentration response curve in the absence and in the presence of the compound of the invention. The distance (mm) between the morphine concentration response curves in the absence and the presence of the compound of the invention was measured, at a contraction inhibition of 50% on the morphine concentration response curve. The Log(CR−1) value of Formula 2 below was determined from a van Rossum summary table based on the distance, and the $pA_2$ value was calculated.

$$\mathrm{Log}(CR-1) = \mathrm{Log}[B] + pA_2 \qquad \text{Formula 2}$$

[B]: Concentrations of compounds of the invention

The antagonistic activities ($pA_2$ values) of compounds of the invention for opioid μ receptors are shown in Table 3.

TABLE 3

Antagonistic activities for opioid μ receptors

| Example No. | $pA_2$ value |
|---|---|
| Example 1-2 | 8.06 |
| Example 2-2 | 8.28 |
| Example 4 | 7.74 |
| Example 5-7 | 6.55 |
| Example 6-4 | 7.91 |
| Example 7-3 | 7.52 |
| Example 8 | 8.15 |
| Example 9-5 | 7.52 |
| Example 10-8 | 7.52 |
| WO03/035645 Ex 2-3 | 8.14 |
| WO03/035645 Ex 3A-3 | 7.64 |
| WO03/035645 Ex 3B-1 | 8.26 |
| WO03/035645 Ex 3G-2 | 8.12 |
| WO03/035645 Ex 2-18 | 8.86 |
| WO03/035645 Ex 5B-1 | 8.66 |
| WO03/035645 Ex 2-17 | 8.38 |

These results demonstrate that the compounds of the invention have antagonistic action on opioid μ receptors. Thus, the compounds of the invention are expected to exhibit effects as therapeutic and prophylactic agents against the side-effects of opioid μ receptor agonists such as constipation, nausea and vomiting, or against idiopathic constipation, postoperative ileus, paralytic ileus and irritable bowel syndrome, by inhibition of opioid μ receptors.

BEST MODE FOR CARRYING OUT THE INVENTION

Formulation examples will now be described.

FORMULATION EXAMPLE 1

| Hard gelatin capsules | |
|---|---|
| Example compound | 20 mg |
| Corn starch | 200 mg |
| Magnesium stearate | 10 mg |
| Total | 230 mg |

The components were uniformly mixed and filled into hard gelatin capsules to prepare hard gelatin capsules containing 460 mg.

FORMULATION EXAMPLE 2

| Hard gelatin capsules | |
|---|---|
| Example compound | 20 mg |
| Corn starch | 89 mg |
| Crystalline cellulose | 89 mg |
| Magnesium stearate | 2 mg |
| Total | 200 mg |

The components were uniformly mixed and filled into hard gelatin capsules to prepare hard gelatin capsules containing 200 mg.

FORMULATION EXAMPLE 3

| Soft gelatin capsules | |
|---|---|
| (Drug solution) | |
| Example compound | 20 mg |
| Medium-chain fatty acid triglyceride | 160 mg |
| Polyoxyethylene hydrogenated castor oil 60 | 20 mg |
| Subtotal | 200 mg |
| (Capsule) | |
| Gelatin | 100 mg |
| Glycerin | 30 mg |
| Methyl paraoxybenzoate | 0.2 mg |
| Propyl paraoxybenzoate | 0.05 mg |
| Purified water | q.s. |
| Subtotal | 140 mg |
| Total | 340 mg |

Each capsule was formed first using a rotary soft capsule maker from the capsule solution heated to dissolution, and then after encapsulating therein the drug solution components which had been uniformly dissolved beforehand, the capsule was shaped and thoroughly dried.

FORMULATION EXAMPLE 4

| Tablets | |
|---|---|
| Example compound | 10 mg |
| Corn starch | 45 mg |
| Crystalline cellulose | 35 mg |
| Polyvinylpyrrolidone (as 10% aqueous solution) | 4 mg |
| Sodium carboxymethylcellulose | 4.5 mg |
| Magnesium stearate | 0.5 mg |
| Talc | 1 mg |
| Total | 100 mg |

The principal agent, starch and cellulose were passed through a sieve and thoroughly mixed. The polyvinylpyrrolidone aqueous solution was combined with the powder and the mixture was passed through a No. 14 mesh sieve. The resulting granules were dried at 50-60° C. and then passed through a No. 18 mesh sieve. Next, the sodium carboxymethylcellulose, magnesium stearate and talc which had already been passed through a No. 60 mesh sieve were added to the granules, and the obtained mixture was supplied to a tableting machine to produce tablets with a unit weight of 100 mg.

FORMULATION EXAMPLE 5

| Tablets | |
|---|---|
| Example compound | 250 mg |
| Crystalline cellulose | 400 mg |
| Thyroid | 10 mg |
| Magnesium stearate | 5 mg |
| Total | 665 mg |

After uniformly mixing the components, a tableting machine was used to produce tablets with a unit weight of 665 mg.

A suspension containing 5 mg of the active ingredient per 5 ml dosage was produced in the following manner.

| Suspension | |
|---|---|
| Example compound | 5 mg |
| Sodium carboxymethylcellulose | 50 mg |
| Simple syrup | 1.25 mL |
| Aqueous benzoic acid solution | 0.10 mL |
| Aromatic agent | q.s. |
| Purified water | To total of 5 mL |
| Total | 5 mL |

The principal agent was passed through a No. 45 mesh sieve and mixed with the sodium carboxymethylcellulose and simple syrup to prepare a paste. The aqueous benzoic acid solution and aromatic agent were diluted in a small amount of purified water and added to the obtained paste while stirring. The purified water was then added to the desired volume.

The present invention will now be further explained through the following examples, which are only illustrative of the invention and are not intended to be restrictive in any way.

PRODUCTION EXAMPLE 1

N-[2-[1-[2-[4-(p-Toluidino)piperidin-1-yl]ethyl]cyclohexyl]ethyl]phthalimide

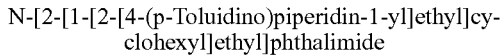

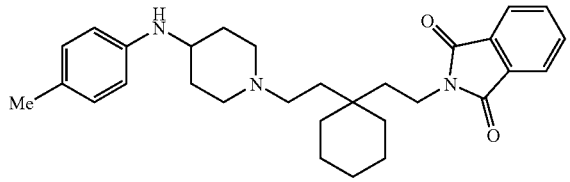

After adding sodium triacetoxyborohydride (0.82 g, 3.85 mmol) to a solution of 4-(p-toluidino)piperidine (0.73 g, 3.85 mmol), N-[2-[1-(formylmethyl)cyclohexyl]ethyl]phthalimide (0.77 g, 2.57 mmol) and acetic acid (0.30 mL, 5.14 mmol) in 1,2-dichloroethane (10 mL), the mixture was stirred at room temperature for 1.5 hours. Saturated aqueous sodium hydrogencarbonate was then added, and extraction was performed with chloroform-ethanol (10:1). After drying (anhydrous sodium sulfate), the solvent was distilled off under reduced pressure. The obtained residue was purified by silica gel column chromatography (25 g Merck Art 9385, chloroform:methanol=20:1) to obtain the title compound as a colorless oil (1.32 g).

$^1$H-NMR (CDCl$_3$) δ: 1.35-1.63 (m, 16H), 2.05-2.08 (m, 2H), 2.15-2.23 (m, 2H), 2.23 (s, 3H), 2.42-2.46 (m, 2H), 2.94-2.98 (m, 2H), 3.25-3.30 (m, 1H), 3.64-3.68 (m, 2H), 6.53 (d, 2H, J=8.3 Hz), 6.97 (d, 2H, J=7.8 Hz), 7.69-7.72 (m, 2H), 7.81-7.86 (m, 2H).

PRODUCTION EXAMPLE 2

N-[2-[1-[2-[4-[N-(p-Tolyl)-2-furancarboxamide]piperidin-1-yl]ethyl]cyclohexyl]ethyl]phthalimide

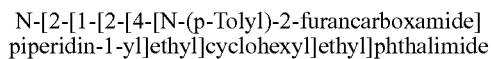

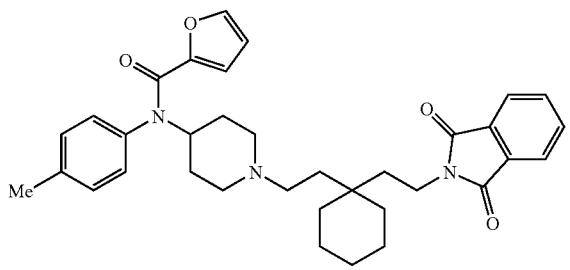

After adding 2-furoyl chloride (0.055 mL, 0.55 mmol) to a solution of N-[2-[1-[2-[4-(p-toluidino)piperidin-1-yl]ethyl]cyclohexyl]ethyl]phthalimide (202 mg, 0.43 mmol) and triethylamine (0.14 mL, 1.00 mmol) in methylene chloride (2 mL), the mixture was stirred at room temperature for 1 hour. The reaction mixture was washed with 10% aqueous citric acid, saturated aqueous sodium hydrogencarbonate and saturated brine in that order, and then dried (anhydrous sodium sulfate) and concentrated under reduced pressure. The obtained residue was purified by silica gel column chromatography (10 g NH Silica Chromatorex DM2035, hexane:ethyl acetate=7:3) to obtain the title compound as a colorless amorphous solid (142 mg) (58% yield).

$^1$H-NMR (CDCl$_3$) δ: 1.25-1.60 (m, 16H), 1.85-1.89 (m, 2H), 2.14-2.21 (m, 2H), 2.35-2.42 (m, 2H), 2.39 (s, 3H), 3.02-3.06 (m, 2H), 3.59-3.64 (m, 2H), 4.75-4.84 (m, 1H), 5.38 (s, 1H), 6.13 (dd, 1H, J=1.5 Hz, 3.4 Hz), 7.02 (d, 2H, J=7.8 Hz), 7.18 (d, 2H, J=7.8 Hz), 7.35 (s, 1H), 7.68-7.70 (m, 2H), 7.81-7.83 (m, 2H).

PRODUCTION EXAMPLE 3

N-[1-[2-[1-(2-Aminoethyl)cyclohexyl]ethyl]piperidin-4-yl]-N-(p-tolyl)-2-furancarboxamide

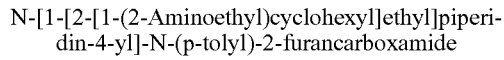

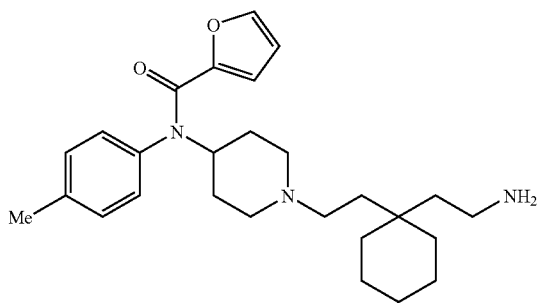

After adding hydrazine monohydrate (0.49 mL, 10.0 mmol) to a suspension of N-[2-[1-[2-[4-[N-(p-tolyl)-2-furancarboxamide]piperidin 1-yl]ethyl]cyclohexyl]ethyl]phthalimide (1.91 g, 3.36 mmol) in ethanol (30 mL), the mixture was heated to reflux for 2.5 hours. The reaction mixture was cooled to room temperature, the insoluble portion was filtered out, and the filtrate was concentrated under reduced pressure. The obtained residue was purified by silica gel column chromatography (25 g NH Silica Chromatorex DM2035, chloroform) to obtain the title compound as a colorless oil (1.64 g) (quantitative).

¹H-NMR (CDCl₃) δ: 1.23-1.57 (m, 16H), 1.83-1.86 (m, 2H), 2.04-2.12 (m, 2H), 2.22-2.27 (m, 2H), 2.39 (s, 3H), 2.59-2.64 (m, 2H), 2.94-2.98 (m, 2H), 4.72-4.81 (m, 1H), 5.37 (s, 1H), 6.13 (dd, 1H, J=2.0 Hz, 3.4 Hz), 7.01 (d, 2H, J=7.8 Hz), 7.17 (d, 2H, J=7.8 Hz), 7.34(d, 1H, J=2.0 Hz).

EXAMPLE 1-1

N-[1-[2-[1-[2-bis(Pyridin-3-ylmethyl)amino]ethyl]cyclohexyl]ethyl]piperidin-4-yl]-N-(p-tolyl)-2-furan-carboxamide

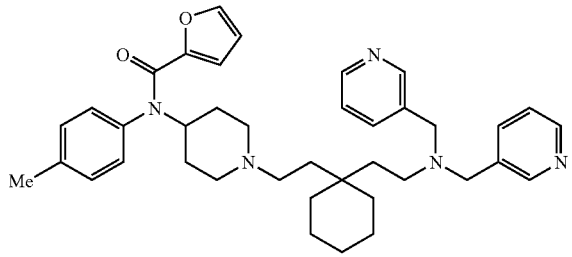

After adding sodium triacetoxyborohydride (212 mg, 1.00 mmol) to a solution of N-[1-[2-[1-(2-aminoethyl)cyclohexyl]ethyl]piperidin-4-yl]-N-(p-tolyl)-2-furancarboxamide (130 mg, 0.30 mmol), 3-pyridinecarboxyaldehyde (80 mg, 0.75 mmol) and acetic acid (70 µL, 1.20 mmol) in 1,2-dichloroethane (5 mL), the mixture was stirred for 18 hours. Saturated aqueous sodium hydrogencarbonate was added to the reaction mixture, and extraction was performed with chloroform. The organic layer was washed with saturated brine and dried (anhydrous sodium sulfate), and then the solvent was distilled off under reduced pressure. The residue was purified by silica gel column chromatography (5 g NH Silica Chromatorex DM2035, chloroform) to obtain the title compound as a colorless oil (178 mg, 0.29 mmol) (96% yield).

¹H-NMR (CDCl₃) δ: 1.13-1.51 (m, 16H), 1.79-1.89 (m, 4H), 2.03-2.08 (m, 2H), 2.35-2.39 (m, 2H), 2.39 (s, 3H), 2.76-2.80 (m, 2H), 3.57 (s, 4H), 4.68-4.76 (m, 1H), 5.37 (s, 1H), 6.14 (dd, 1H, J=1.5 Hz, 3.4 Hz), 7.00 (d, 2H, J=7.8 Hz), 7.17 (d, 2H, J=8.3 Hz), 7.24-7.29 (m, 2H), 7.35 (d, 1H, J=1.5 Hz), 7.67-7.70 (m, 2H), 8.51 (dd, 2H, J=2.0 Hz, 4.9 Hz), 8.56 (d, 1H, J=2.0 Hz).

EXAMPLE 1-2

N-[1-[2-[1-1-[2-[bis(Pyridin-3-ylmethyl)amino]ethyl]cyclohexyl]ethyl]piperidin-4-yl]-N-(p-tolyl)-2-furancarboxamide tetrahydrochloride

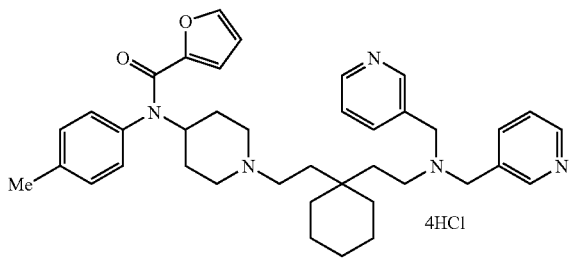

After adding a 4N hydrochloric acid/ethyl acetate solution (0.35 mL, 1.4 mmol) to a solution of N-[1-[2-[1-[2-[bis(pyridin-3-ylmethyl)amino]ethyl]cyclohexyl]ethyl]piperidin-4-yl]-N-(p-tolyl)-2-furancarboxamide (178 mg, 0.29 mmol) in ethyl acetate (2 mL)-ethanol (2 mL), the mixture was stirred at room temperature for 20 minutes. The reaction mixture was concentrated under reduced pressure, ethyl acetate was added to the obtained residue, and the precipitated crystals were filtered out and dried under reduced pressure to obtain the title compound as a white solid (197 mg, 0.26 mmol) (89% yield).

¹H-NMR (DMSO-d₆) δ: 1.04-2.03 (m, 10H), 2.39 (s, 3H), 2.98-3.07 (m, 4H), 3.45-3.54 (m, 2H), 4.74-4.80 (m, 1H), 5.40 (s, 1H), 6.33 (dd, 1H, J=1.5 Hz, 3.4 Hz), 7.17 (d, 2H, J=8.3 Hz), 7.30 (d, 2H, J=8.3 Hz), 7.67 (s, 1H), 7.82 (brs, 2H), 8.57 (d, 2H, J=7.8 Hz), 8.80 (d, 2H, J=4.9 Hz), 9.04 (brs, 2H), 10.22 (br, 1H).

EXAMPLE 2-1

N-[1-[2-[1-[2-[bis(Pyridin-4-ylmethyl)amino]ethyl]cyclohexyl]ethyl]piperidin-4-yl]-N-(p-tolyl)-2-furan-carboxamide

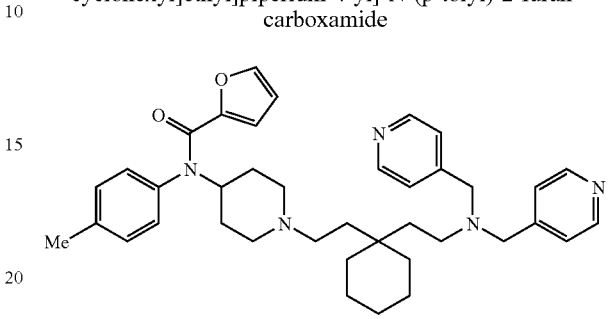

After adding sodium triacetoxyborohydride (212 mg, 1.00 mmol) to a solution of N-[1-[2-[1-(2-aminoethyl)cyclohexyl]ethyl]piperidin-4-yl]-N-(p-tolyl)-2-furancarboxamide (131 mg, 0.30 mmol), 4-pyridinecarboxyaldehyde (80 mg, 0.75 mmol) and acetic acid (70 µL, 1.20 mmol) in 1,2-dichloroethane (5 mL), the mixture was stirred for 18 hours. Saturated aqueous sodium hydrogencarbonate was added to the reaction mixture, and extraction was performed with chloroform. The organic layer was washed with saturated brine and dried (anhydrous sodium sulfate), and then the solvent was distilled off under reduced pressure. The residue was purified by silica gel column chromatography (5 g NH Silica Chromatorex DM2035, chloroform) to obtain the title compound as a colorless oil (171 mg, 0.28 mmol) (92% yield).

¹H-NMR (CDCl₃) δ: 1.13-1.52 (m, 16H), 1.81-1.85 (m, 2H), 1.94-2.00 (m, 2H), 2.08-2.13 (m, 2H), 2.35-2.39 (m, 2H), 2.39 (s, 3H), 2.79-2.82 (m, 2H), 3.57 (s, 4H), 4.69-4.77 (m, 1H), 5.37 (s, 1H), 6.14 (dd, 1H, J=1.5 Hz, 3.4 Hz), 7.00 (d, 2H, J=8.3 Hz), 7.17 (d, 2H, J=8.3 Hz), 8.54 (dd, 1H, J=1.5 Hz, 4.4 Hz), 7.29-7.35 (m, 5H).

EXAMPLE 2-2

N-[1-[2-[1-[2-[bis(Pyridin-4-ylmethyl)amino]ethyl]cyclohexyl]ethyl]piperidin-4-yl]-N-(p-tolyl)-2-furan-carboxamide tetrahydrochloride

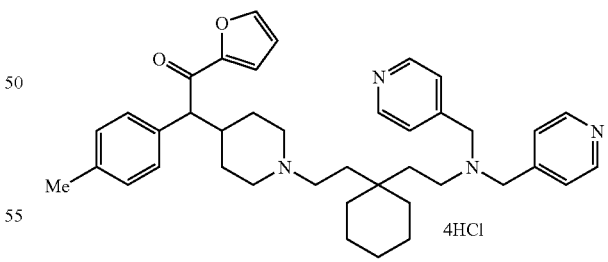

After adding a 4N hydrochloric acid/ethyl acetate solution (0.35 mL, 1.4 mmol) to a solution of N-[1-[2-[1-[2-[bis(pyridin-4-ylmethyl)amino]ethyl]cyclohexyl]ethyl]piperidin-4-yl]-N-(p-tolyl)-2-furancarboxamide (171 mg, 0.28 mmol) in ethyl acetate (2 mL)-ethanol (2 mL), the mixture was stirred at room temperature for 10 minutes. Ethyl acetate (3 mL) was added to the reaction mixture, and after stirring for 20 minutes in an ice bath, the precipitated crystals were filtered out and dried under reduced pressure to obtain the title compound as a white solid (136 mg, 0.18 mmol) (64% yield).

$^1$H-NMR (DMSO-d$_6$) δ: 1.08-1.75 (m, 16H), 1.98-2.03 (m, 2H), 2.38 (s, 3H), 2.50-2.55 (m, 2H), 2.79-2.86 (m, 2H), 3.04-3.10 (m, 2H), 3.38-3.51 (m, 2H), 4.04 (brs, 4H), 4.73-4.83 (m, 1H), 5.41 (s, 1H), 6.33 (dd, 1H, J=1.5 Hz, 3.4 Hz), 7.16 (d, 2H, J=8.3 Hz), 7.30 (d, 2H, J=8.3 Hz), 7.66 (s, 1H), 8.01 (d, 4H, J=3.0 Hz), 8.82 (brs, 4H), 9.99 (br, 1H).

EXAMPLE 3-1

N-[1-[2-[1-[2-(1-Oxo-2-isoindolinyl)ethyl]cyclohexyl]ethyl]piperidin-4-yl]-N-(p-tolyl)-2-furancarboxamide

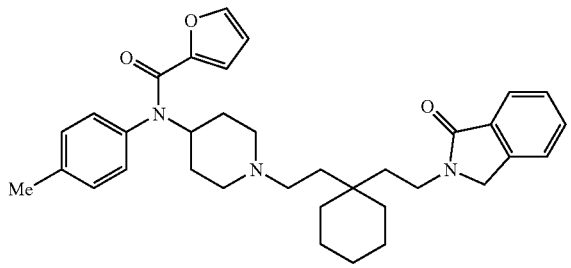

After adding methyl 2-formylbenzoate (254 mg, 1.55 mmol), acetic acid (89 μL, 1.55 mmol) and sodium triacetoxyborohydride (265 mg, 1.25 mmol) to a solution of N-[1-[2-[1-(2-aminoethyl)cyclohexyl]ethyl]piperidin-4-yl]-N-(p-tolyl)-2-furancarboxamide (226 mg, 0.52 mmol) in 1,2-dichloroethane (3 mL), the mixture was stirred at room temperature for 3 hours. The reaction mixture was diluted with chloroform and washed with saturated aqueous sodium hydrogencarbonate and saturated brine in that order. The organic layer was dried (anhydrous sodium sulfate) and concentrated under reduced pressure, and the obtained residue was purified by silica gel column chromatography (10 g NH Silica Chromatorex DM2035, hexane:ethyl acetate=7:3-1:1) to obtain the title compound as a colorless oil (194 mg, 0.26 mmol) (67% yield).

$^1$H-NMR (CDCl$_3$) δ: 1.30-1.60 (m, 16H), 1.87 (d, 2H, J=12.2 Hz), 2.14 (t, 2H, J=11.2 Hz), 2.31-2.36 (m, 2H), 3.02 (d, 2H, J=11.7 Hz), 3.53-3.58 (m, 2H), 4.36 (s, 2H), 4.73-4.82 (m, 1H), 5.35 (brs, 1H), 6.13 (dd, 1H, J=1.5 Hz, 2.9 Hz), 7.02 (d, 2H, J=8.3 Hz), 7.18 (d, 2H, J=8.3 Hz), 7.35 (d, 1H, J=1.0 Hz), 7.42-7.47 (m, 2H), 7.50-7.54 (m, 1H), 7.83 (d, 1H, J=7.3 Hz).

EXAMPLE 3-2

N-[1-[2-[1-[2-(1-Oxo-2-isoindolinyl)ethyl]cyclohexyl]ethyl]piperidin-4-yl]-N-(p-tolyl)-2-furancarboxamide hydrochloride

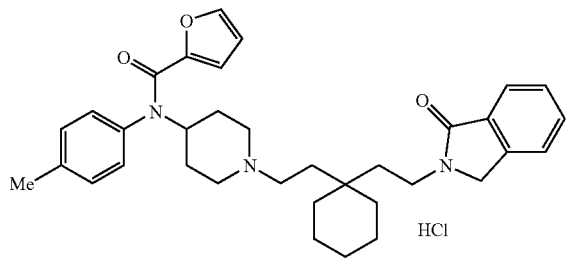

After dissolving N-[1-[2-[1-[2-(1-oxo-2-isoindolinyl)ethyl]cyclohexyl]ethyl]piperidin-4-yl]-N-(p-tolyl)-2-furancarboxamide (167 mg, 0.30 mmol) in ethyl acetate:ethanol=1:1 (4 mL), a 4N hydrochloric acid/ethyl acetate solution (0.25 mL, 1.00 mmol) was added. The reaction mixture was stirred at room temperature for 5 minutes and then concentrated under reduced pressure. The obtained residue was dissolved in ethanol (10 mL) and the solution was concentrated under reduced pressure to about 0.5 mL, after which 2-propanol (10 mL) was added and the mixture was concentrated under reduced pressure to obtain the title compound as a light brown amorphous substance (124 mg, 0.21 mmol) (70% yield).

$^1$H-NMR (DMSO-d$_6$) δ: 1.26-1.47 (m, 10H), 1.50-1.55 (m, 2H), 1.69-1.78 (m, 4H), 2.04-2.07 (m, 2H), 3.00-3.20 (m, 4H), 3.47-3.61 (m, 4H), 4.51 (s, 2H), 4.78-4.85 (m, 1H), 5.51 (d, 1H, J=3.4 Hz), 6.32 (dd, 1H, J=2.0 Hz, 3.4 Hz), 7.17 (d, 2H, J=8.3 Hz), 7.31 (d, 2H, J=8.3 Hz), 7.45-7.49 (m, 1H), 7.57-7.61 (m, 2H), 7.63-7.67 (m, 2H), 9.57 (br, 1H).

EXAMPLE 4

N-[1-[2-[1-[2-(2,4-Dihydroxybenzylamino)ethyl]cyclohexyl]ethyl]piperidin-4-yl]-N-(p-tolyl)-2-furancarboxamide dihydrochloride

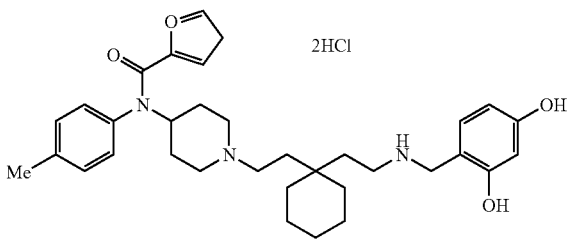

After adding acetic acid (34 μL, 0.57 mmol) and sodium triacetoxyborohydride (121 mg, 0.57 mmol) to a solution of N-[1-[2-[1-(2-aminoethyl)cyclohexyl]ethyl]piperidin-4-yl]-N-(p-tolyl)-2-furancarboxamide (100 mg, 0.23 mmol) and 2,4-dihydroxybenzaldehyde (79 mg, 0.57 mmol) in 1,2-dichloroethane (3 mL), the mixture was stirred at room temperature for 16 hours. Saturated brine was added to the reaction mixture, and extraction was performed with chloroform:ethanol=9:1. The organic layer was dried (anhydrous sodium sulfate), and then the solvent was distilled off under reduced pressure. The residue was purified by silica gel column chromatography (10 g NH Silica Chromatorex DM2035, chloroform:methanol=50:1) to obtain a colorless oil (49 mg, 0.09 mmol) (38% yield). The oil was dissolved in ethyl acetate (3 mL), and a 4N hydrochloric acid/ethyl acetate solution (0.1 mL, 0.40 mmol) was added. After stirring for 30 minutes at room temperature and then for 30 minutes while cooling on ice, the precipitated crystals were filtered out and dried under reduced pressure to obtain the title compound as colorless crystals (43 mg, 0.07 mmol) (78% yield).

$^1$H-NMR (DMSO-d$_6$) δ: 1.16-1.26 (m, 4H), 1.31-1.46 (m, 6H), 1.51-1.77 (m, 6H), 2.02-2.06 (m, 2H), 2.36 (s, 3H), 2.71-2.89 (m, 2H), 2.98-3.16 (m, 4H), 3.53-3.57 (m, 2H), 3.94 (brs, 2H), 4.76-4.80 (m, 1H), 5.49 (d, 1H, J=2.9 Hz), 6.25 (dd, 1H, J=2.4 Hz, 8.3 Hz), 6.31-6.33 (m, 1H), 6.41 (d, 1H, J=2.0 Hz), 7.15-7.18 (m, 3H), 7.30 (d, 2H, J=8.3 Hz), 7.62 (d, 1H, J=1.0 Hz), 7.92 (br, 1H), 8.71 (br, 1H), 9.45 (s, 1H), 9.72 (br, 1H), 9.89 (s, 1H).

IR (KBr) cm$^{-1}$: 3407, 2928, 2644, 1619, 1556, 1511, 1469, 1407, 1342, 1312, 1188, 1111, 757.

EXAMPLE 5-1

1-[1-[2-(tert-Butyldiphenylsiloxy)ethyl]cyclohexyl]acetaldehyde

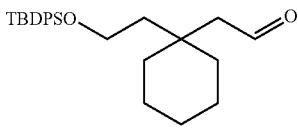

After adding 2,2,6,6-tetramethylpiperidine 1-oxyl free radical (31 mg, 0.20 mmol) to a solution of 2-[1-[2-(tert-butyldiphenylsiloxy)ethyl]cyclohexyl]ethanol (810 mg, 1.97 mmol) and iodobenzene diacetate (700 mg, 2.17 mmol) in methylene chloride (10 mL), the mixture was stirred at room temperature for 4 hours. The reaction mixture was washed with saturated aqueous sodium hydrogencarbonate and saturated brine in that order and dried (anhydrous sodium sulfate), and then the solvent was distilled off under reduced pressure to obtain the title compound as a brown oil (1.29 g). This was used without purification for the following step.

$^1$H-NMR (CDCl$_3$) δ: 1.03 (s, 9H), 1.33-1.45 (m, 10H), 1.77 (t, 2H, J=6.8 Hz), 2.34 (d, 2H, J=2.9 Hz), 3.76 (t, 2H, J=7.3 Hz), 7.31-7.45 (m, 6H), 7.65-7.71 (m, 4H), 9.78 (t, 1H, J=2.9 Hz).

EXAMPLE 5-2

4-[2-[1-[2-(tert-Butyldiphenylsiloxy)ethyl]cyclohexyl]ethyl]morpholine

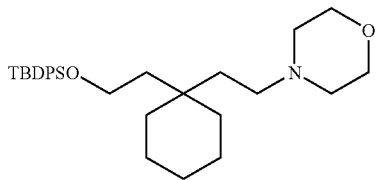

After adding sodium triacetoxyborohydride (0.63 g, 2.98 mmol) to a solution of 1-[1-[2-(tert-butyldiphenylsiloxy)ethyl]cyclohexyl]acetaldehyde (1.29 g, ca. 1.97 mmol), morpholine (0.26 mL, 2.98 mmol) and acetic acid (0.23 mL, 4.02 mmol) in 1,2-dichloroethane (5 mL), the mixture was stirred at room temperature for 2.5 hours. Saturated aqueous sodium hydrogencarbonate was added to the reaction mixture and extraction was performed with chloroform. The organic layer was washed with saturated brine and dried (anhydrous sodium sulfate), and then the solvent was distilled off under reduced pressure to obtain the title compound as a brown oil (1.31 g). This was used without purification for the following step.

$^1$H-NMR (CDCl$_3$) δ: 1.04 (s, 9H), 1.18-1.37 (m, 12H), 1.59 (t, 2H, J=7.8 Hz), 2.15-2.20 (m, 2H), 2.32 (brs, 4H), 3.65-3.73 (m, 6H), 7.31-7.45 (m, 6H), 7.63-7.72 (m, 4H).

EXAMPLE 5-3

4-[2-[1-(2-Hydroxyethyl)cyclohexyl]ethyl]morpholine

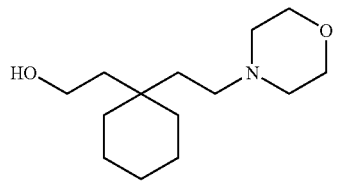

After adding concentrated hydrochloric acid (0.5 mL, 6.0 mmol) to a solution of 4-[2-[1-[2-(tert-butyldiphenylsiloxy)ethyl]cyclohexyl]ethyl]morpholine (1.31 g, ca. 1.97 mmol) in methanol (10 mL) at room temperature, the mixture was stirred for 4.5 hours. The reaction mixture was then concentrated under reduced pressure, 1N hydrochloric acid (10 mL) was added to the obtained residue, and extraction was performed with diethyl ether. After adding 5N aqueous sodium hydroxide to the aqueous layer to adjust the pH to 12, extraction was performed with diethyl ether. The organic layer was dried (anhydrous sodium sulfate) and then the solvent was distilled off under reduced pressure to obtain the title compound as a colorless oil (448 mg) (94% yield, 2 steps).

$^1$H-NMR (CDCl$_3$) δ: 1.26-1.61 (m, 14H), 2.32 (t, 2H, J=6.8 Hz), 2.47 (brs, 4H), 3.40 (br, 1H), 3.66-3.72 (m, 6H).

EXAMPLE 5-4

4-[2-[1-(Formylmethyl)cyclohexyl]ethyl]morpholine

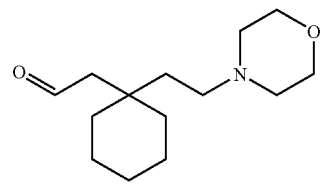

After adding 2,2,6,6-tetramethylpiperidine 1-oxyl free radical (32 mg, 0.20 mmol) to a solution of 4-[2-[1-(2-hydroxyethyl)cyclohexyl]ethyl]morpholine (439 mg, 1.82 mmol) and iodobenzene diacetate (644 mg, 2.00 mmol) in methylene chloride (10 mL), the mixture was stirred at room temperature for 14 hours. The reaction mixture was washed with saturated aqueous sodium hydrogencarbonate and saturated brine in that order and dried (anhydrous sodium sulfate), and then the solvent was distilled off under reduced pressure to obtain the title compound as a brown oil (625 mg). This was used without purification for the following step.

$^1$H-NMR (CDCl$_3$) δ: 1.31-1.67 (m, 12H), 2.32-2.52 (m, 6H), 3.66-3.72 (m, 6H), 9.80 (s, 1H).

EXAMPLE 5-5

4-[2-[1-[2-[4-(p-Toluidino)piperidin-1-yl]ethyl]cyclohexyl]ethyl]morpholine

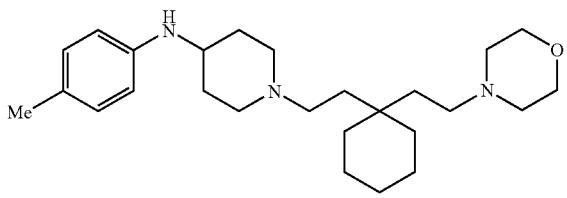

After adding sodium triacetoxyborohydride (579 mg, 2.73 mmol) to a solution of 4-[2-[1-(formylmethyl)cyclohexyl]ethyl]morpholine (625 mg, ca. 1.82 mmol), 4-(p-toluidino)piperidine (519 mg, 2.73 mmol) and acetic acid (0.21 mL, 3.64 mmol) in 1,2-dichloroethane (10 mL), the mixture was stirred for 3 hours. Saturated aqueous sodium hydrogencarbonate was added to the reaction mixture, and extraction was performed with chloroform. The organic layer was washed with saturated brine and dried (anhydrous sodium sulfate), and then the solvent was distilled off under reduced pressure. The residue was purified by silica gel column chromatography (30 g Merck Art 9385, chloroform:methanol=1:0-10:1) to obtain the title compound as a colorless oil (346 mg) (48% yield).

¹H-NMR (CDCl₃) δ: 1.24-1.53 (m, 16H), 2.00-2.46 (m, 15H), 2.89-2.92 (m, 2H), 3.23-3.31 (m, 1H), 3.66-3.74 (m, 2H), 3.73 (s, 3H), 6.52 (d, 2H, J=8.3 Hz), 6.97 (d, 2H, J=7.8 Hz).

EXAMPLE 5-6

N-[1-[2-[1-[2-(Morpholino)ethyl]cyclohexyl]ethyl]piperidin-4-yl]-N-(p-tolyl)-2-furancarboxamide

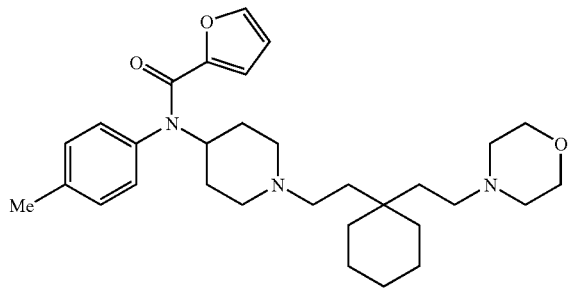

After adding triethylamine (0.21 mL, 1.50 mmol) and 2-furoyl chloride (0.10 mL, 1.00 mmol) in that order to a solution of 4-[2-[1-[2-[4-(p-toluidino)piperidin-1-yl]ethyl]cyclohexyl]ethyl]morpholine (319 mg, 0.77 mmol) in methylene chloride (5 mL) while cooling on ice, the mixture was stirred at room temperature for 16 hours. The reaction mixture was concentrated under reduced pressure, and the obtained residue was purified by silica gel column chromatography (20 g Merck Art 9385, chloroform:methanol=20:1-chloroform:methanol:ammonia water=10:1:0.1) to obtain the title compound as a colorless oil (283 mg) (72% yield).

¹H-NMR (CDCl₃) δ: 1.24-1.57 (m, 16H), 1.84-1.87 (m, 2H), 2.07-2.13 (m, 2H), 2.23-2.30 (m, 4H), 2.39 (s, 3H), 2.39-2.46 (m, 4H), 2.95-2.98 (m, 2H), 3.69-3.72 (m, 4H), 4.73-4.81 (m, 1H), 5.38 (d, 1H, J=2.4 Hz), 6.13 (dd, 1H, J=1.5 Hz, 3.4 Hz), 7.01 (d, 2H, J=8.3 Hz), 7.18 (d, 2H, J=8.3 Hz), 7.34 (s, 1H).

EXAMPLE 5-7

N-[1-[2-[1-[2-(Morpholino)ethyl]cyclohexyl]ethyl]piperidin-4-yl]-N-(p-tolyl)-2-furancarboxamide dihydrochloride

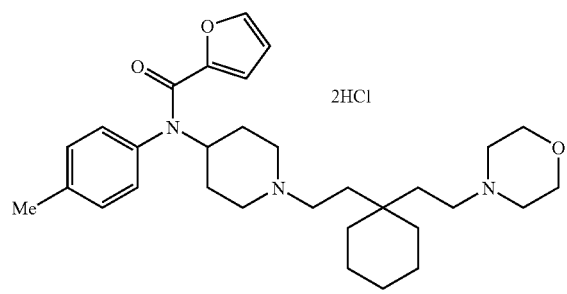

After adding a 4N hydrochloric acid/ethyl acetate solution (0.5 mL, 2.0 mmol) to a solution of N-[1-[2-[1-[2-(morpholino)ethyl]cyclohexyl]ethyl]piperidin-4-yl]-N-(p-tolyl)-2-furancarboxamide (283 mg, 0.56 mmol) in ethyl acetate (4 mL), the mixture was stirred at room temperature for 10 minutes (producing a white precipitate). Ethanol (0.5 mL) was added to the reaction mixture (to dissolve the precipitate), and the solution was concentrated under reduced pressure to obtain the title compound as a white amorphous solid (283 mg) (87% yield).

¹H-NMR (DMSO-d₆) δ: 1.17-1.47 (m, 10H), 1.57-1.77 (m, 6H), 1.99-2.03 (m, 2H), 2.39 (s, 3H), 3.01-3.15 (m, 8H), 3.43-3.46 (m, 2H), 3.59-3.62 (m, 2H), 3.78-3.81 (m, 2H), 3.84-3.96 (m, 2H), 4.75-4.81 (m, 1H), 5.39 (s, 1H), 6.33 (dd, 1H, J=1.5 Hz, 3.4 Hz), 7.16 (d, 2H, J=7.8 Hz), 7.30 (d, 2H, J=8.3 Hz), 7.66 (s, 1H), 10.22 (brs, 1H), 11.38 (brs, 1H).

MS (ESI) m/z: 508 (M+H)⁺.

EXAMPLE 6-1

1-(3-Cyclohexyl-3-hydroxypropyl)-4-(5-methylpyridin-2-yl)aminopiperidine

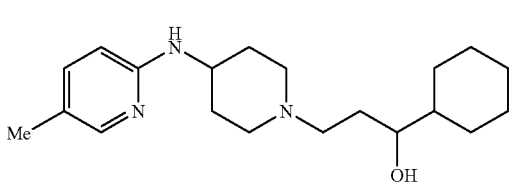

A mixture of 4-(5-methylpyridin-2-yl)aminopiperidine (394 mg, 2 mmol), sodium hydrogencarbonate (277 mg, 3.2 mmol) and 3-cyclohexyl-3-hydroxypropyl 4-bromobenzenesulfonate (932 mg, 2.4 mmol) in 1,2-dimethoxyethane (10 mL) was refluxed for 8 hours. After then adding 5 g of NH silica Chromatorex DM1020 to the reaction mixture, it was concentrated under reduced pressure. The residue was purified by silica gel column chromatography (60 g NH silica Chromatorex DM2035, hexane:ethyl acetate=1:1) to obtain the title compound as a light yellow solid (405 mg) (59.6% yield).

¹H-NMR(CDCl₃)δ: 0.94-1.06 (m, 2H), 1.07-1.34 (m, 4H), 1.40-1.80 (m, 8H), 1.90-2.08 (m, 4H), 2.16 (s, 3H), 2.28-2.40 (m, 1H), 2.54-2.68 (m, 2H), 2.74-2.88 (m, 1H), 3.02-3.15 (m, 1H), 3.46-3.53 (m, 1H), 3.57-3.68 (m, 1H), 4.12-4.22 (m, 1H), 6.29 (d, 1H, J=8.8 Hz), 7.22 (dd, 1H, J=2.0 Hz, 8.8 Hz), 7.89 (d, 1H, J=2.0 Hz)

EXAMPLE 6-2

1-(3-tert-Butyldimethylsiloxy-3-cyclohexylpropyl)-4-(5-methylpyridin-2-yl)aminopiperidine

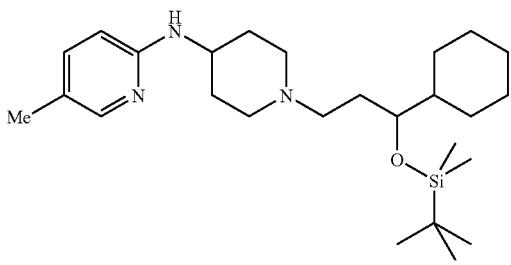

After adding tert-butyldimethylsilyl chloride (203 mg, 1.5 mmol) to a solution of 1-(3-cyclohexyl-3-hydroxypropyl)-4-(5-methylpyridin-2-yl)aminopiperidine (405 mg, 1.22 mmol), triethylamine (0.20 mL) and 4-dimethylaminopyridine (30 mg, 0.24 mmol) in methylene chloride (5 mL) while cooling on ice, the mixture was stirred at room temperature for 18 hours. Triethylamine (0.20 mL), 4-dimethylaminopyridine (30 mg, 1.5 mmol) and tert-butyldimethylsilyl chloride (203 mg, 1.5 mmol) were further added to the reaction mixture and stirring was continued at room temperature for 70 hours. NH silica Chromatorex DM1020 was added to the reaction mixture, which was then concentrated under reduced pressure. The residue was purified by silica gel column chromatography (60 g NH silica Chromatorex DM2035, hexane:ethyl acetate=4:1) to obtain the title compound as a colorless oil (423 mg) (77.7% yield).

¹H-NMR(CDCl₃)δ: 0.030 (s, 3H), 0.033 (s, 3H), 0.89 (s, 9H), 0.85-1.25 (m, 5H), 1.30-1.40 (m, 1H), 1.39-1.56 (m,

2H), 1.57-1.78 (m, 7H), 2.00-2.08 (m, 2H), 2.08-2.20 (m, 2H), 2.16 (s, 3H), 2.28-2.47 (m, 2H), 2.80-2.88(m, 2H), 3.44-3.50 (m, 1H), 3.52-3.64 (m, 1H), 4.23 (brd, 1H, J=8.0 Hz), 6.30 (d, 1H, J=8.3 Hz), 7.23 (dd, 1H, J=2.0 Hz, 8.3 Hz), 7.88 (d, 1H, J=2.0 Hz)

EXAMPLE 6-3

N-[1-(3-tert-Butyldimethylsiloxy-3-cyclohexylpropyl)piperidin-4-yl]-N-(5-methylpyridin-2-yl)-2-furancarboxamide

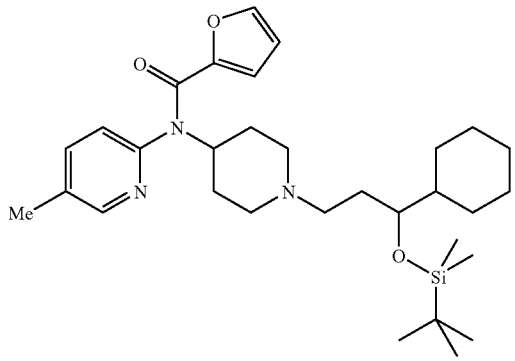

After adding 2-furoyl chloride (0.14 mL, 1.4 mmol) dropwise to a solution of 1-(3-tert-butyldimethylsiloxy-3-cyclohexylpropyl)-4-(5-methylpyridin-2-yl)aminopiperidine (423 mg, 0.95 mmol) and triethylamine (0.264 mL) in methylene chloride (4 mL) while cooling on ice, the mixture was stirred at room temperature for 18 hours. NH silica Chromatorex DM1020 was added to the reaction mixture, which was then concentrated under reduced pressure. The residue was purified by silica gel column chromatography (60 g NH silica Chromatorex DM2035, hexane:ethyl acetate=4:1) to obtain the title compound as an oil (458 mg) (89.4% yield).

$^{1}$H-NMR(CDCl$_{3}$)δ: 0.00 (s, 6H), 0.86 (s, 9H), 0.80-1.37 (m, 6H), 1.50-1.66 (m, 7H), 1.67-1.75 (m, 2H), 1.89-1.96 (m, 2H), 2.06-2.15 (m, 2H), 2.22-2.31 (m, 1H), 2.38 (s, 3H), 2.36-2.45 (m, 1H), 2.90-2.96 (m, 2H), 3.37-3.44 (m, 1H), 4.73 (tt, 1H, J=4.0 Hz, 12.3 Hz), 5.93 (d, 1H, J=3.4 Hz), 6.18 (dd, 1H, J=1.5 Hz, 3.4 Hz), 6.98 (d, 1H, J=7.8 Hz), 7.22 (d, 1H, J=1.5 Hz), 7.50 (dd, 1H, J=2.5 Hz, 7.8 Hz), 8.37 (d, 1H, J=2.5 Hz)

EXAMPLE 6-4

N-[1-(3-Cyclohexyl-3-hydroxypropyl)piperidin-4-yl]-N-(5-methylpyridin-2-yl)-2-furancarboxamide hydrochloride

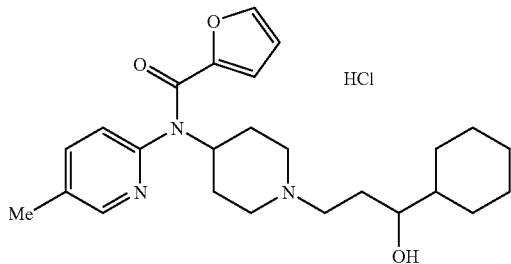

After adding tetrabutylammonium fluoride (1.0 M THF solution, 2 mL) to a solution of N-[1-(3-tert-butyldimethylsiloxy-3-cyclohexylpropyl)piperidin-4-yl]-N-(5-methylpyridin-2-yl)-2-furancarboxamide (423 mg, 0.95 mmol) in THF (5 mL), the mixture was stirred at room temperature for 18 hours. Tetrabutylammonium fluoride (1.0 M THF solution, 2 mL) was further added to the reaction mixture and stirring was continued at 50° C. for 8 hours. The reaction mixture was concentrated under reduced pressure, and the residue was purified by silica gel column chromatography (100 g Merck Art 9385, chloroform:methanol=20:1) to obtain the free form of the title compound as light pink crystals (264 mg) (73.2% yield). The crystals were dissolved in 5.0 mL of ethyl acetate, and addition of 0.4 mL of a 4N-hydrochloric acid-ethyl acetate solution resulted in precipitation of the crystals. The crystals were filtered to obtain the target substance as a light pink solid (164 mg) (41.8% yield).

$^{1}$H-NMR(CDCl3)δ: 0.92-1.38 (m, 6H), 1.59-1.78 (m, 4H), 1.80-1.95 (m, 3H), 2.24-2.42 (m, 4H), 2.48 (s, 3H), 2.82-2.94 (m, 2H), 3.09-3.22 (m, 2H), 3.51-3.65 (m, 2H), 3.74-3.81 (m, 1H), 4.95-5.05 (m, 1H), 6.26-6.33 (m, 2H), 7.20-7.23 (m, 1H), 7.27 (d, 1H, J=7.8 Hz), 7.84 (dd, 1H, J=2.0 Hz, 7.8 Hz), 8.44 (d, 1H, J=2.0 Hz), 11.15 (brs, 1H)

MS (ESI) m/z: 426 (M+H)$^{+}$

EXAMPLE 7-1

Methyl 3-hydroxymethyltricyclo[3.3.1.1$^{3,7}$]decane-1-carboxylate

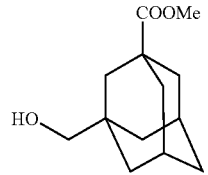

After dissolving dimethyl 1,3-adamantanedicarboxylate (1.00 g, 3.96 mmol) in tetrahydrofuran (5 mL), diisobutylaluminum hydride (0.95 M; 5.0 mL, 4.75 mmol) was added dropwise while cooling on ice, and then the mixture was further stirred for 3 hours while cooling on ice. After the reaction, water (0.2 mL) and then aqueous 15% NaOH (0.2 mL) were added dropwise at room temperature, and the mixture was stirred for 30 minutes. Next, water (0.6 mL) and anhydrous magnesium sulfate were added and stirred therewith, and the insoluble portion was filtered out. The solvent was distilled off under reduced pressure, and the obtained residue was subjected to chromatography (50 g Merck Art. 9385, hexane:ethyl acetate=3:2) to obtain the title compound as a colorless oil (0.1648 g, 0.735 mmole) (19% yield).

$^{1}$H-NMR (DMSO-d$_{6}$) δ: 1.39-1.41 (m, 4H), 1.54 (s, 2H), 1.55-1.65 (m, 2H), 1.66-1.80 (m, 4H), 2.00-2.07 (m, 2H), 3.02 (d, 2H, J=5.9 Hz), 3.57 (s, 3H), 4.29 (t, 1H, J=5.9 Hz).

EXAMPLE 7-2

Methyl 3-[4-(5-methylpyridin-2-yl)aminopiperidin-1-ylmethyl]tricyclo[3.3.1.1$^{3,7}$]decane--1-carboxylate

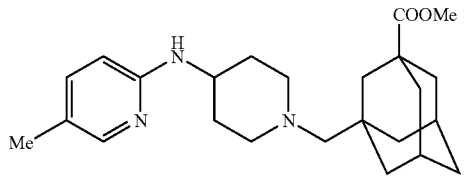

After dissolving methyl 3-hydroxymethyltricyclo[3.3.1.1$^{3,7}$]decane-1-carboxylate (0.1648 g, 0.735 mmol) and pyri dine (0.0829 g, 1.05 mmol) in methylene chloride (5 mL), trifluoromethanesulfonic anhydride (0.185 mL, 1.11 mmol) was added dropwise while cooling on ice and the mixture was stirred for 1 hour. Water (10 mL) was added to the reaction mixture, and after extraction with ethyl acetate (20 mL), the extract was washed with 1N HCl (10 mL), saturated aqueous NaHCO$_3$ (10 mL) and brine (10 mL) in that order and dried over anhydrous magnesium sulfate, and then 4-(5-methylpyridin-2-yl)aminopiperidine (0.2995 g, 1.57 mmol) was mixed therewith and the solvent was distilled off under reduced pressure. The obtained yellow oil was heated at 60° C. for 1 hour. It was then subjected to chromatography (50 g Merck Art. 9385, methylene chloride:methanol:ammonia water=97:3:0.2) to obtain the title compound as a white solid (0.2398 g, 0.603 mmole) (82% yield).

$^1$H-NMR (DMSO-d$_6$) δ: 1.35-1.48 (m, 6H), 1.51-1.63 (m, 4H), 1.68-1.83 (m, 6H), 1.98 (s, 2H), 1.89-2.06 (m, 2H), 2.07 (s, 3H), 2.22-2.31 (m, 2H), 2.63-2.71 (m, 2H), 3.51-3.61 (m, 1H), 3.58 (s, 3H), 5.90 (d, 1H, J=7.8 Hz), 6.35 (d, 1H, J=8.3 Hz), 7.14 (dd, 1H, J=2.0 Hz, 8.3 Hz), 7.75 (d, 1H, J=2.0 Hz).

EXAMPLE 7-3

N-[1-[(3-Methoxycarbonyl-1-tricyclo[3.3.1.1$^{3,7}$]decyl)methyl]piperidin-4-yl]-N-(5-methylpyridin-2-yl)-2-furancarboxamide hydrochloride

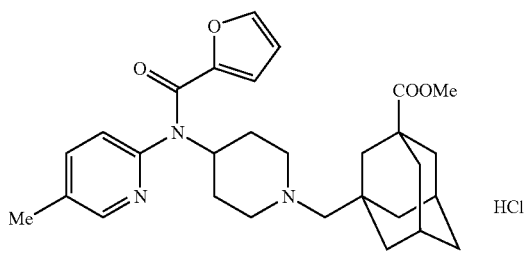

After dissolving methyl 3-[4-(5-methylpyridin-2-yl)aminopiperidin-1-ylmethyl]tricyclo[3.3.1.1$^{3,7}$]decane-1-carboxylate (0.2248 g, 0.565 mmol) in methylene chloride (5 mL), triethylamine (0.12 g, 1.21 mmol) was added at room temperature. Next, 2-furoyl chloride (0.071 mL, 0.724 mmol) was added dropwise while cooling on ice, and the mixture was stirred at room temperature for 16 hours. The reaction mixture was then subjected to chromatography (100 g Merck Art. 9385, methylene chloride:methanol:ammonia water=98:2:0.1-97:3:0.2) without pretreatment, to obtain the free form of the title compound as a colorless oil (0.2675 g, 0.544 mmol) (96% yield). This was further subjected to hydrochloride salification to obtain the title compound as a white solid (0.2951 g, 0.522 mmol) (96% yield).

$^1$H-NMR (DMSO-d$_6$) δ: 1.55-1.66 (m, 6H), 1.67-1.80 (m, 6H), 1.90-2.10 (m, 6H), 2.37 (s, 3H), 2.83-2.90 (m, 2H), 3.21-3.41 (m, 2H), 3.45-3.52 (m, 2H), 3.59 (s, 3H), 4.69-4.80 (m, 1H), 5.87-5.94 (m, 1H), 6.34-6.36 (m, 1H), 7.24-7.28 (m, 1H), 7.55-7.56 (m, 1H), 7.73-7.77 (m, 1H), 8.39-8.41 (m, 1H)

IR (KBr) cm$^{-1}$: 2919, 1725, 1644, 1627, 1239, 754

MS (ESI) m/z: 492 (M+H)$^+$.

EXAMPLE 8

[1-[2-[4-[N-(5-Methylpyridin-2-yl)-2-furancarboxamide]piperidin-1-yl]ethyl]cyclohexyl]acetic diethylphosphonocarboximidic anhydride trihydrochloride

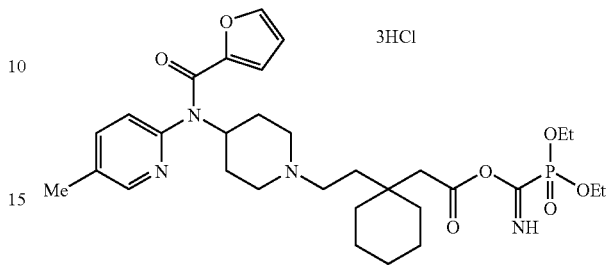

After dissolving [1-[2-[4-[N-(5-methylpyridin-2-yl)-2-furancarboxamide]piperidin-1-yl]ethyl]cyclohexyl]acetic acid (0.2004 g, 0.442 mmol) in N,N-dimethylformamide (4 mL), diethyl phosphorocyanidate (0.2170 g, 1.33 mmol), triethylamine (0.1628 g, 1.61 mmol) and 2-amino-2-hydroxymethyl-1,3-propanediol (0.0877 g, 0.724 mmol) were added and the mixture was stirred at room temperature for 5 days. Ethyl acetate (50 mL) was added to the reaction mixture, and then after washing with water (20 mL×2) and drying over anhydrous magnesium sulfate, the solvent was distilled off under reduced pressure and the obtained residue was subjected to chromatography (50 g Merck Art. 9385, methylene chloride:methanol:ammonia water=95:5:0.3) to obtain the free form of the title compound as a colorless oil (0.1543 g, 0.250 mmol) (57% yield). This was further subjected to hydrochloride salification to obtain the title compound as a white solid (0.1630 g, 0.224 mmol) (90% yield).

$^1$H-NMR (DSMO-d$_6$) δ:1.20-1.38 (m, 11H), 1.45-1.59 (m, 3H), 1.78-1.98 (m, 6H), 1.99-2.08 (m, 2H), 2.37 (s, 3H), 2.90-3.00 (m, 2H), 3.03-3.16 (m, 2H), 3.42-3.51 (m, 2H), 4.15-4.27 (m, 4H), 4.69-4.80 (m, 1H), 5.90 (d, 1H, J=3.4 Hz), 5.99 (s, 1H), 6.35 (dd, 1H, J=2.0 Hz, 3.4 Hz), 7.23 (d, 1H, J=7.8 Hz), 7.55 (d, 1H, J=2.0 Hz), 7.73 (dd, 1H, J=2.5 Hz, 7.8 Hz), 8.39 (d, 1H, J=2.4 Hz), 9.69-9.82 (br, 1H); IR (KBr) cm$^{-1}$: 3444, 2995, 2936, 2503, 1650, 1620, 1556, 1472, 1327, 1294, 1273, 1029, 993, 977, 771

MS (ESI) m/z: 599 (M+H)$^+$.

EXAMPLE 9-1 tert-Butyl 4-(mesitylamino)piperidine-1-carboxylate

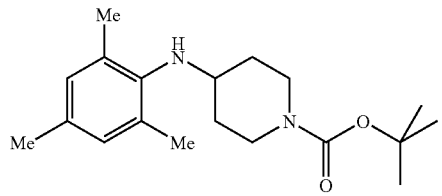

After adding sodium triacetoxyborohydride (7.98 g, 37.6 mmol) to a solution of tert-butyl 4-oxopiperidine-1-carboxylate (5.00 g, 25.1 mmol), 2,4,6-trimethylaniline (3.56 g, 26.3 mmol) and acetic acid (2.9 mL, 50.2 mmol) in methylene chloride (50 mL), the mixture was stirred at room temperature for 3.5 hours. Saturated aqueous sodium hydrogencarbonate (150 mL) was added to the reaction mixture, which was then stirred until bubbling settled. The organic layer was separated and the aqueous layer was extracted with chloroform (100 mL). The organic layers were combined, washed with saturated brine (100 mL) and dried (Na$_2$SO$_4$), and then the solvent was distilled off under reduced pressure. The residue was purified by silica gel column chromatography (50 g Merck Art. 9385, hexane:ethyl acetate=9: 1) to obtain the title compound as a brown oil (5.71 g) (71% yield).

$^1$H-NMR (CDCl$_3$) δ: 1.24-1.42 (m, 2H), 1.46 (s, 9H), 1.87-1.91 (m, 2H), 2.16 (s, 6H), 2.21 (s, 3H), 2.68-2.73 (m, 2H), 2.96-3.02 (m, 1H), 4.08 (br, 2H), 6.81 (s, 2H).

EXAMPLE 9-2

4-(Mesitylamino)piperidine

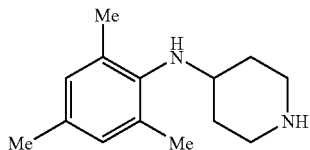

After adding trifluoroacetic acid (10 mL) to a solution of tert-butyl 4-(mesitylamino)piperidine-1-carboxylate (5.71 g, 17.9 mmol) in methylene chloride (30 mL), the mixture was stirred at room temperature for 22 hours and then concentrated under reduced pressure. The residue was dissolved in methanol (10 mL), toluene (20 mL) was added, and concentration under reduced pressure was repeated. The residue was purified by silica gel column chromatography (75 g NH silica Chromatorex DM2035, hexane:ethyl acetate=4:1-1:1-chloroform:methanol=10:1) to obtain the title compound as a brown solid (3.57 g) (65% yield, 2 steps).

$^1$H-NMR (CDCl$_3$) δ: 1.74-1.85 (m, 2H), 2.11-2.18 (m, 2H), 2.23 (s, 3H), 2.24 (s, 6H), 2.86 (br, 2H), 3.09-3.19 (m, 1H), 3.41-3.49 (m, 2H), 6.83 (s, 2H).

EXAMPLE 9-3

Methyl [1-[2-[4-(mesitylamino)piperidin-1-yl]ethyl]cyclohexyl]acetate

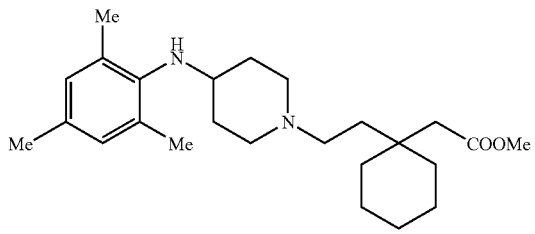

A suspension of 4-(mesitylamino)piperidine (250 mg, 1.15 mmol), methyl [1-(2-bromoethyl)cyclohexyl]acetate (371 mg, 1.38 mmol) and potassium carbonate (318 mg, 2.3 mmol) in N,N-dimethylformamide (3 mL) was stirred at 80° C. for 10 hours. Chloroform (10 mL) was added to the reaction mixture, the insoluble portion was filtered out, and the filtrate was concentrated under reduced pressure. The residue was dissolved in xylene (10 mL) and concentrated under reduced pressure. The residue was then purified by silica gel column chromatography (10 g Merck Art 9385, hexane:ethyl acetate=7:3-chloroform:methanol=10:1) to obtain the title compound as a brown oil (243 mg) (53% yield).

$^1$H-NMR (CDCl$_3$) δ: 1.37-1.47 (m, 12H), 1.58-1.62 (m, 2H), 1.89-1.97 (m, 4H), 2.23 (s, 6H), 2.23 (s, 3H), 2.29 (s, 2H), 2.32-2.35 (m, 2H), 2.88-2.96 (m, 3H), 3.63 (s, 3H), 6.80 (s, 2H).

EXAMPLE 9-4

Methyl [1-[2-[4-(N-mesityl-2-furancarboxamide)piperidin-1-yl]ethyl]cyclohexyl]acetate

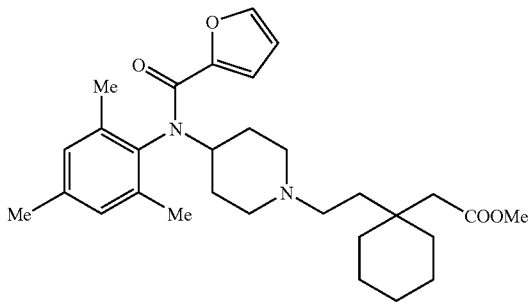

After adding 2-furoyl chloride (0.11 mL, 1.12 mmol) dropwise to a solution of methyl [1-[2-[4-(mesitylamino)piperidin-1-yl]ethyl]cyclohexyl]acetate (225 mg, 0.56 mmol) and triethylamine (0.23 mL, 1.68 mmol) in methylene chloride (1 mL) while cooling on ice, the mixture was stirred at room temperature for 4 hours. The reaction mixture was diluted with chloroform (2 mL), washed with saturated aqueous sodium hydrogencarbonate (2 mL), 10% aqueous citric acid (2 mL) and saturated brine (2 mL) in that order and dried (Na$_2$SO$_4$), and then the solvent was distilled off under reduced pressure. The residue was purified by silica gel column chromatography (15 g NH silica Chromatorex DM2035, hexane:ethyl acetate=4:1) to obtain the title compound as a white solid (187 mg) (68% yield).

$^1$H-NMR (CDCl$_3$) δ: 1.32-1.58 (m, 14H), 1.99-2.11 (m, 4H), 2.13 (s, 6H), 2.28 (s, 2H), 2.32 (s, 3H), 2.30-2.35 (m, 2H), 2.94-2.98 (m, 2H), 3.62 (s, 3H), 4.26-4.34 (m, 1H), 5.23 (d, 1H, J=3.9 Hz), 6.13 (dd, 1H, J=2.0 Hz, 3.9 Hz), 6.91 (s, 2H), 7.52 (s, 1H).

EXAMPLE 9-5

[1-[2-[4-(N-Mesityl-2-furancarboxamide)piperidin-1-yl]ethyl]cyclohexyl]acetic acid hydrochloride

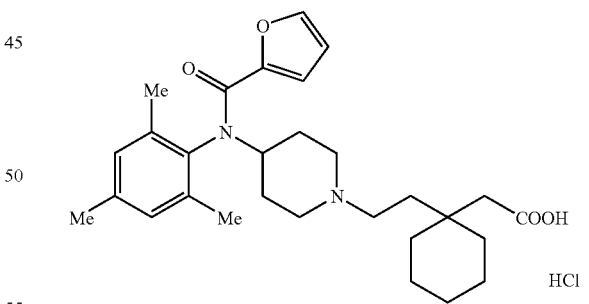

After adding 2N aqueous sodium hydroxide (1.6 mL, 3.2 mmol) to a solution of methyl [1-[2-[4-(N-mesityl-2-furancarboxamide)piperidin-1-yl]ethyl]cyclohexyl]acetate (159 mg, 0.32 mmol) in methanol (10 mL), the mixture was stirred at room temperature for 13 hours. A 2N aqueous sodium hydroxide solution (1.0 mL, 2.0 mmol) was added to the reaction mixture, which was then stirred at room temperature for 24 hours and at 40° C. for 2 hours. Acetic acid (0.35 mL) was added to the reaction mixture, and after concentration under reduced pressure, the obtained residue was extracted with chloroform:ethanol (100:20 v/v, 10 mL×3) and the organic layer was dried (Na$_2$SO$_4$) and concentrated under reduced pressure to obtain the free form of the title compound as a white solid (229 mg).

This was further subjected to hydrochloride salification to obtain the title compound (148 mg) (90% yield, 2 steps).

$^1$H-NMR (DMSO-d$_6$) δ:1.23-1.42 (m, 10H), 1.75-1.82 (m, 2H), 1.87-2.04 (m, 4H), 2.12 (s, 6H), 2.17 (s, 2H), 2.29 (s, 3H), 2.98-3.08 (m, 4H), 3.46-3.49 (m, 2H), 4.30-4.37 (m, 1H), 5.34 (brs, 1H), 6.31-6.32 (m, 1H), 7.02 (s, 2H), 7.68 (s, 1H), 10.25 (br, 1H)

IR (KBr) cm$^{-1}$: 3444, 2931, 2854, 2638, 2537, 1733, 1713, 1633, 1557, 1469, 1392, 1351, 1313, 1238, 1187, 1037, 751

MS (ESI) m/z: 481 (M+H)$^+$.

EXAMPLE 10-1

2-[1-(2-Hydroxyethyl)cyclohexyl]ethanol

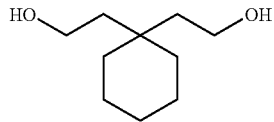

After suspending lithium aluminum hydride (11.4 g, 0.300 mol) in tetrahydrofuran (300 mL), a solution of 1,1-cyclohexanediacetic acid (30.0 g, 0.150 mol) in tetrahydrofuran (200 mL) was added dropwise at room temperature. After completion of the dropwise addition, the mixture was stirred for 5 minutes while cooling on ice, and then water (11.5 mL) was added dropwise over a period of 5 minutes while cooling on ice. After stirring for 10 minutes, 15% aqueous sodium hydroxide (11.5 mL) was added dropwise over a period of 5 minutes. Diethyl ether (500 mL, special grade) was added, and after stirring for 5 minutes, water (34.5 mL) was added. The mixture was then stirred for 2 hours while cooling on ice, and then celite was added and the mixture was filtered. The filtrate was concentrated under reduced pressure and azeotropically distilled with toluene to obtain the title compound as a colorless oil (21.7 g).

$^1$H-NMR (CDCl$_3$) δ:1.23-1.50 (m, 10H), 1.64 (t, 4H, J=7.2 Hz), 1.96-2.17 (m, 2H), 3.72 (t, 4H, J=7.2 Hz).

EXAMPLE 10-2

2-[1-(2-tert-Butyldiphenylsiloxyethyl)cyclohexyl]ethanol

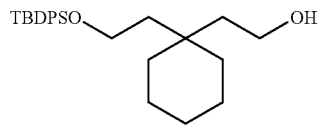

tert-Butylchlorodiphenylsilane (34.4 mL, 0.132 mol) was added dropwise to a solution of 2-[1-(2-hydroxyethyl)cyclohexyl]ethanol (21.7 g, 0.126 mol) in methylene chloride (280 mL) while cooling on ice. After stirring the mixture for 14 hours at room temperature, 25% aqueous ammonium chloride (300 mL) was added and extraction was performed. The organic layer was washed with saturated aqueous sodium chloride, and then the organic layer was dried over anhydrous magnesium sulfate, filtered and concentrated under reduced pressure. The obtained residue was purified by silica gel column chromatography (500 g Merck Art. 9385, hexane: ethyl acetate=4:1) to obtain the title compound as a colorless oil (36.8 g) (2 steps, 60% yield).

$^1$H-NMR (CDCl$_3$) δ:1.05 (s, 9H), 1.19-1.43 (m, 10H), 1.48-1.55 (m, 3H), 1.61 (t, 2H, J=7.6 Hz), 3.56 (t, 2H, J=7.6 Hz), 3.70 (t, 2H, J=7.6 Hz), 7.35-7.47 (m, 6H), 7.64-7.73 (m, 4H).

EXAMPLE 10-3

2-[1-(2-tert-Butyldiphenylsiloxyethyl)cyclohexyl]ethyl methanesulfonate

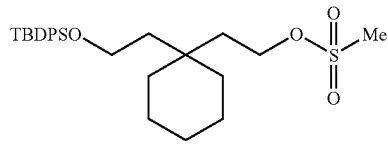

After adding triethylamine (2.20 mL, 15.8 mmol) to a solution of 2-[1-(2-tert-butyldiphenylsiloxyethyl)cyclohexyl]ethanol (3.24 g, 7.80 mmol) in methylene chloride (25 mL), methanesulfonyl chloride (0.91 mL, 11.7 mmol) was added dropwise while cooling on ice. The mixture was stirred at room temperature for 40 minutes, and then saturated aqueous sodium hydrogencarbonate (300 mL) was added, extraction was performed with chloroform and the organic layer was washed with saturated aqueous sodium chloride. The organic layer was dried over anhydrous magnesium sulfate, filtered, and then concentrated under reduced pressure to obtain the title compound as a yellow oil (3.97 g).

$^1$H-NMR (CDCl$_3$) δ:1.04 (s, 9H), 1.58-1.61 (m, 2H), 1.73 (t, 2H, J=7.3 Hz), 2.92 (s, 3H), 3.69 (t, 2H, J=7.3 Hz), 4.20 (t, 2H, J=7.8 Hz), 7.37-7.46 (m, 6H), 7.66-7.68 (m, 4H).

EXAMPLE 10-4 tert-Butyl-2-(1-ethylcyclohexyl)ethoxydiphenylsilane

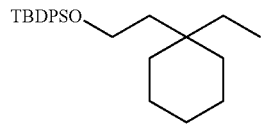

After suspending lithium aluminum hydride (0.30 g, 7.80 mmol) in tetrahydrofuran (15 mL), a solution of 2-[1-(2-tert-butyldiphenylsiloxyethyl)cyclohexyl]ethyl methanesulfonate (3.97 g, 7.80 mmol) in tetrahydrofuran (10 mL) was added dropwise at room temperature over a period of 10 minutes. After stirring for an additional 10 minutes, the mixture was heated to reflux for 45 minutes. Water (0.30 mL), 15% aqueous sodium hydroxide (0.30 mL) and water (0.90 mL) were added dropwise in that order while cooling on ice, diethyl ether (25 mL) was added and the mixture was stirred for 16 hours, and then celite was added and stirring was continued for 1 hour prior to filtration. The filtrate was concentrated under reduced pressure to obtain the title compound as a colorless oil (3.02 g).

$^1$H-NMR (CDCl$_3$) δ:0.67 (t, 3H, J=7.3 Hz), 1.07 (s, 9H), 1.20-1.46 (m, 14H), 1.58-1.73 (m, 2H), 3.69 (t, 2H, J=7.3 Hz), 7.34-7.44 (m, 6H), 7.65-7.69 (m, 4H).

EXAMPLE 10-5

2-(1-Ethylcyclohexyl)ethanol

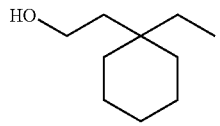

After adding a 1.0 M tetrabutylammonium fluoride-tetrahydrofuran solution (7.70 mL, 7.70 mmol) to a solution of tert-butyl-2-(1-ethylcyclohexyl)ethoxydiphenylsilane (3.02 g, 7.65 mmol) in tetrahydrofuran (20 mL) at room temperature, the mixture was stirred for 2 hours. A 1.0 M tetrabutylammonium fluoride tetrahydrofuran solution (7.70 mL, 7.70 mmol) was then added, and the mixture was stirred for 14 hours. After further adding 1N hydrochloric acid (20 mL) to the reaction mixture, extraction was performed with ethyl acetate. The organic layer was washed with saturated aqueous sodium chloride, and the organic layer was dried over anhydrous magnesium sulfate. After filtering and concentration under reduced pressure, the obtained residue was purified by silica gel column chromatography (100 g Merck Art. 9385, hexane:ethyl acetate=6:1) to obtain the title compound as a colorless oil (708 mg) (3 steps, 57% yield).

$^1$H-NMR (CDCl$_3$) δ:0.80 (t, 3H, J=7.8 Hz), 1.22-1.32 (m, 6H), 1.36-1.45 (m, 6H), 1.54-1.60 (m, 2H), 1.60-1.65 (m, 1H), 3.65 (t, 2H, J=7.8 Hz).

EXAMPLE 10-6

(1-Ethylcyclohexyl)acetaldehyde

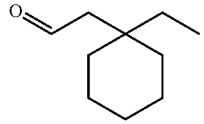

After adding iodobenzene diacetate (1.61 g, 4.98 mmol) to a solution of 2-(1-ethylcyclohexyl)ethanol (708 mg, 4.53 mmol) in methylene chloride (15 mL) at room temperature, 2,2,6,6-tetramethylpiperidine 1-oxyl free radical (70.8 mg, 0.450 mmol) was added and the mixture was stirred for 15 hours. Diethyl ether was added to the reaction mixture, which was then washed with 10% aqueous sodium thiosulfate, 1N hydrochloric acid and saturated aqueous sodium hydrogencarbonate in that order. The organic layer was dried over anhydrous magnesium sulfate, filtered and concentrated under reduced pressure to obtain the title compound as an orange oil (1.54 g).

$^1$H-NMR (CDCl$_3$) δ:0.86 (t, 3H, J=7.8 Hz), 1.39-1.50 (m, 12H), 2.32 (d, 2H, J=2.9 Hz), 9.84 (t, 1H, J=3.4 Hz).

EXAMPLE 10-7

1-[2-(1-Ethylcyclohexyl)ethyl]-4-(5-methylpyridin-2-yl)aminopiperidine

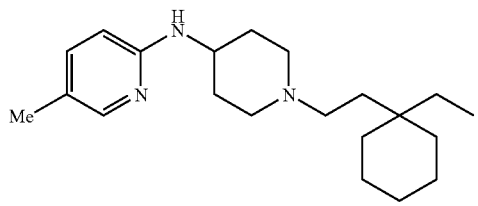

After adding triethylamine (1.30 mL, 9.06 mmol) to a solution of 4-(5-methylpyridin-2-yl)aminopiperidine dihydrobromide (1.60 g, 4.53 mmol) in 1,2-dichloroethane (7 mL) and stirring the mixture for 30 minutes, a solution of (1-ethylcyclohexyl)acetaldehyde (1.54 g, 4.53 mmol) in 1,2-dichloroethane (8 mL) was added and the mixture was stirred for 15 minutes. Sodium triacetoxyborohydride (0.96 g, 4.53 mmol) was then added while cooling on ice, and after stirring the mixture for 5 minutes, it was further stirred at room temperature for 1 hour. A 25% aqueous ammonium chloride solution, chloroform and 3N aqueous sodium hydroxide were added to the reaction mixture, extraction was performed with chloroform, and the organic layer was washed with saturated aqueous sodium chloride. The organic layer was then dried over anhydrous magnesium sulfate, filtered and concentrated under reduced pressure. The obtained residue was purified by silica gel column chromatography (100 g Merck Art. 9385, chloroform:methanol=95:5) to obtain the title compound as a brown oil (1.37 g, 4.16 mmol) (2 steps, 92% yield).

$^1$H-NMR (CDCl$_3$) δ:0.77 (t, 3H, J=7.8 Hz), 1.21-1.30 (m, 5H), 1.35-1.48 (m, 8H), 1.48-1.60 (m, 2H), 2.06 (d, 2H, J=13.6 Hz), 2.13-2.19 (m, 2H), 2.16 (s, 3H), 2.26-2.30 (m, 2H), 2.90 (d, 2H, J=10.8 Hz), 3.55-3.63 (m, 1H), 4.24 (d, 1H, J=8.3 Hz), 6.30 (d, 1H, J=8.3 Hz), 7.23 (dd, 2H, J=2.4 Hz, 8.3 Hz), 7.89 (s, 1H).

MS (ESI) m/z: 330 (M+H)$^+$.

EXAMPLE 10-8

N-[1-[2-(1-Ethylcyclohexyl)ethyl]piperidin-4-yl]-N-(5-methylpyridin-2-yl)-2-furancarboxamide

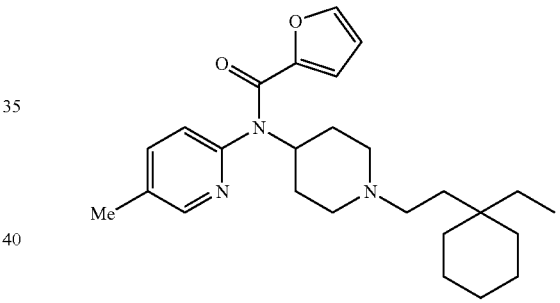

Triethylamine (1.33 mL, 9.55 mmol) was added to a solution of 1-[2-(1-ethylcyclohexyl)ethyl]-4-(5-methylpyridin-2-yl)aminopiperidine (1.31 g, 3.98 mmol) in methylene chloride (13 mL). After adding 2-furoyl chloride (0.47 mL, 4.78 mmol) while cooling on ice, the mixture was stirred for 2 hours. A 25% aqueous ammonium chloride solution was added to the reaction mixture, extraction was performed with chloroform, and the organic layer was washed with saturated aqueous sodium chloride. The organic layer was dried over anhydrous magnesium sulfate, filtered, and concentrated under reduced pressure. The obtained residue was purified by silica gel column chromatography (80 g NH silica Chromatorex DM2035, hexane:ethyl acetate=2:1) to obtain the title compound as a light yellow solid (1.52 g, 3.59 mmol) (90% yield).

$^1$H-NMR (CDCl$_3$) δ:0.74 (t, 3H, J=7.8 Hz), 1.18-1.33 (m, 6H), 1.36-1.40 (m, 8H), 1.56-1.66 (m, 2H), 1.95 (d, 2H, J=12.2 Hz), 2.08 (t, 2H, J=12.2 Hz), 2.20-2.24 (m, 2H), 2.40 (s, 3H), 2.99 (d, 2H, J=11.7 Hz), 4.74 (tt, 1H, J=4.3 Hz, 12.2 Hz), 5.92 (d, 1H, J=7.8 Hz), 6.19 (d, 1H, J=1.9 Hz, 3.4 Hz), 6.99 (d, 1H, J=7.8 Hz), 7.22 (d, 1H, J=1.5 Hz), 7.50 (dd, 1H, J=2.4 Hz, 8.3 Hz), 8.38 (d, 1H, J=1.5 Hz).

MS (ESI) m/z: 424 (M+H)$^+$.

EXAMPLE 11-1

N-[1-[2-[1-(4-Methoxy-3-methoxymethylbutyl)cyclohexyl]ethyl]piperidin-4-yl]-N-(5-methylpyridin-2-yl)-2-furancarboxamide

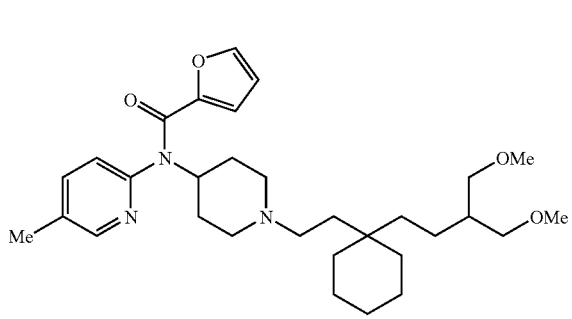

After adding sodium hydride (60% dispersion in mineral oil) (179 mg, 4.47 mmol) to a solution of N-[1-[2-[1-(4-hydroxy-3-hydroxymethylbutyl)cyclohexyl]ethyl]piperidin-4-yl]-N-(5-methylpyridin-2-yl)-2-furancarboxamide (1.00 g, 2.01 mmol) in N,N-dimethylformamide (3 mL) while cooling on ice, the mixture was stirred for 40 minutes. Next, methyl iodide (0.15 mL, 2.41 mmol) was added, stirring was continued for 1 hour, and saturated aqueous sodium hydrogencarbonate (10 mL) was added. Extraction was performed with ethyl acetate, and the extract was washed with saturated aqueous sodium chloride (10 mL) and then dried over anhydrous magnesium sulfate. The residue obtained after filtering and concentration under reduced pressure was purified by silica gel column chromatography (150 g NH silica Chromatorex DM2035, hexane:ethyl acetate=1:1-chloroform:methanol=8:2) to obtain the title compound (100 mg) and a furancarboxylic acid ester of N-[1-[2-[1-(4-methoxy-3-hydroxymethylbutyl)cyclohexyl]ethyl]piperidin-4-yl]-N-(5-methylpyridin-2-yl)-2-furancarboxamide (91 mg).

N-[1-[2-[1-(4-methoxy-3-methoxymethylbutyl)cyclohexyl]ethyl]piperidin-4-yl]-N-(5-methylpyridin-2-yl)-2-furancarboxamide $^1$H-NMR (CDCl$_3$) δ:1.18-1.30 (m, 8H), 1.30-1.45 (m, 8H), 1.57-1.66 (m, 2H), 1.66-1.75 (m, 1H), 1.94 (d, 2H, J=11.2 Hz), 2.06 (t, 2H, J=11.7 Hz), 2.22-2.25 (m, 2H), 2.38 (s, 3H), 2.97 (d, 2H, J=11.7 Hz), 3.29-3.37 (m, 10H), 4.73 (tt, 1H, J=3.9 Hz, 8.3 Hz), 5.93 (d, 1H, J=3.4 Hz), 6.19 (dd, 1H, J=1.0 Hz, 3.4 Hz), 7.00 (d, 1H, J=7.8 Hz), 7.22 (d, 1H, J=1.5 Hz), 7.51 (dd, 1H, J=2.5 Hz, 7.8 Hz), 8.37 (d, 1H, J=2.5 Hz).

Furancarboxylic acid ester of N-[1-[2-[1-(4-methoxy-3-hydroxymethylbutyl)cyclohexyl]ethyl]piperidin-4-yl]-N-(5-methylpyridin-2-yl)-2-furancarboxamide $^1$H-NMR (CDCl$_3$) δ:1.20-1.45 (m, 16H), 1.54-1.62 (m, 2H), 1.89-2.04 (m, 4H), 1.89-1.97 (m, 1H), 2.13-2.22 (m, 2H), 2.38 (s, 3H), 2.94 (d, 2H, J=11.7 Hz), 3.33 (s, 3H), 3.39 (d, 2H, J=6.4 Hz), 4.27 (dd, 1H, J=5.4 Hz, 10.7 Hz), 4.34 (dd, 1H, J=5.4 Hz, 10.7 Hz), 4.71 (t, 1H, J=8.3 Hz), 5.90 (d, 1H, J=3.4 Hz), 6.19 (dd, 1H, J=2.0 Hz, 3.4 Hz), 6.55 (dd, 1H, J=1.9 Hz, 3.4 Hz), 6.90 (d, 1H, J=7.8 Hz), 7.16 (dd, 1H, J=1.0 Hz, 3.4 Hz), 7.23 (d, 1H, J=1.0 Hz), 7.51 (dd, 1H, J=2.5 Hz, 7.8 Hz), 8.37 (d, 1H, J=2.5 Hz).

EXAMPLE 11-2

N-[1-[2-[1-(4-Methoxy-3-hydroxymethylbutyl)cyclohexyl]ethyl]piperidin-4-yl]-N-(5-methylpyridin-2-yl)-2-furancarboxamide

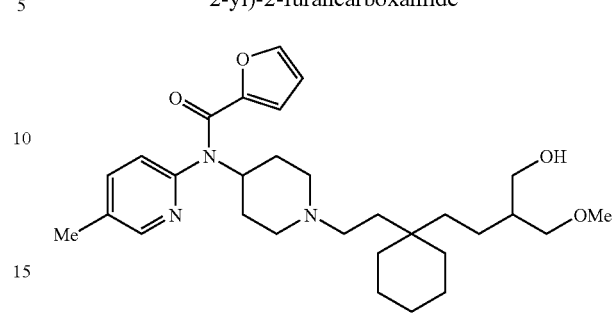

After adding 3N aqueous potassium hydroxide (0.5 mL, 1.50 mmol) to a solution of the furancarboxylic acid ester of N-[1-[2-[1-(4-methoxy-3-hydroxymethylbutyl)cyclohexyl]ethyl]piperidin-4-yl]-N-(5-methylpyridin-2-yl)-2-furancarboxamide (60 mg, 0.10 mmol) in methanol (1.5 mL), the mixture was stirred for 2 hours. After completion of the reaction, water was added, extraction was performed with ethyl acetate, and the organic layer was washed with saturated aqueous sodium chloride and then dried over anhydrous magnesium sulfate. The residue obtained after filtering and concentration under reduced pressure was purified by silica gel column chromatography (30 g NH silica Chromatorex DM2035, ethyl acetate) to obtain the title compound as a colorless amorphous solid (58 mg, 0.10 mmol) (quantitative yield).

$^1$H-NMR (CDCl$_3$) δ:1.10-1.26 (m, 8H), 1.28-1.38 (m, 8H), 1.57-1.66 (m, 2H), 1.63-1.88 (m, 2H), 1.94 (d, 2H, J=11.7 Hz), 2.05-2.12 (m, 2H), 2.16-2.22 (m, 2H), 2.38 (s, 3H), 2.97 (m, 2H), 3.34 (s, 3H), 3.35-3.38 (m, 1H), 3.51 (dd, 1H, J=3.9 Hz, 8.8 Hz), 3.59 (dd, 1H, J=6.8 Hz, 10.7 Hz), 3.67 (dd, 1H, J=3.9Hz, 10.7 Hz), 4.73 (t, 1H, J=12.2 Hz), 5.93 (d, 1H, J=3.4 Hz), 6.19 (dd, 1H, J=1.5 Hz, 3.4 Hz), 6.99 (d, 1H, J=8.3 Hz), 7.22 (d, 1H, J=1.5 Hz), 7.50 (dd, 1H, J=1.5 Hz, 7.8 Hz), 8.37 (d, 1H, J=2.0 Hz

INDUSTRIAL APPLICABILITY

The novel 4-(2-furoyl)aminopiperidine derivatives obtained according to the invention are useful for the prevention and treatment of itching or pruritus in both humans and animals caused by hypersensitivity reaction, such as reaction against insect-inflicted wounds such as flea bites and reaction against environmental allergens including house dust mites and pollen, as well as skin infection by bacteria and fungi or external parasite infection or accompanying renal dialysis.

What is claimed is:

1. A compound or a pharmaceutically acceptable salt thereof, which is selected from the group of compounds consisting of:
   N-[1-[2-[1-[2-[bis(pyridin-3-ylmethyl)amino]ethyl]cyclohexyl]ethyl]piperidin-4-yl]-N-(p-tolyl)-2-furancarboxamide,
   N-[1-[2-[1-[2-[bis(pyridin-4-ylmethyl)amino]ethyl]cyclohexyl]ethyl]piperidin-4-yl]-N-(p-tolyl)-2-furancarboxamide,
   N-[1-[2-[1-[2-(1-oxo-2-isoindolinyl)ethyl]cyclohexyl]ethyl]piperidin-4-yl]-N-(p-tolyl)-2-furancarboxamide,
   N-[1-[2-[1-[2-(2,4-dihydroxybenzylamino)ethyl]cyclohexyl]ethyl]piperidin-4-yl]-N-(p-tolyl)-2-furancarboxamide, N-[1-[2-[1-[2-(morpholino)ethyl]cyclohexyl]ethyl]piperidin-4-yl]-N-(p-tolyl)-2-furancarboxamide, N-[1-(3-cyclohexyl-3-hydroxypropyl)piperidin-4-yl]-N-(5-methylpyridin-2-yl)-2-furancarboxamide, N-[1-[(3-methoxycarbonyl-1-tricyclo[3.3.1.1$^{3,7}$]decyl)methyl]piperidin-4-yl]-N-(5-methylpyridin-2-yl)-2-furancarboxamide,

[1-[2-[4-[N-(5-methylpyridin-2-yl)-2-furancarboxamide]piperidin-1-yl]ethyl]cyclohexyl]acetic diethylphosphonocarboximidic anhydride,

[1-[2-[4-(N-mesityl-2-furancarboxamide)piperidin-1-yl]ethyl]cyclohexyl]acetic acid, N-[1-[2-(1-ethylcyclohexyl)ethyl]piperidin-4-yl]-N-(5-methylpyridin-2-yl)-2-furancarboxamide, N-[1-[2-[1-(4-methoxy-3-methoxymethylbutyl)cyclohexyl]ethyl]piperidin-4-yl]-N-(5-methylpyridin-2-yl)-2-furancarboxamide, and N-[1-[2-[1-(4-methoxy-3-hydroxymethylbutyl)cyclohexyl]ethyl]piperidin-4-yl]-N-(5-methylpyridin-2-yl)-2-furancarboxamide.

2. A medicine comprising as an active ingredient a compound or a pharmaceutically acceptable salt thereof according to claim 1, in combination with pharmaceutically acceptable additives if necessary.

3. A medicine according to claim 2, which is a therapeutic agent for pruritus.

4. A medicine according to claim 3, wherein the pruritus is pruritus caused by reaction against insect-inflicted wounds, reaction against environmental allergens, skin infection by bacteria or fungi or infection by external parasites, or pruritus accompanying renal dialysis.

\* \* \* \* \*